(12) United States Patent
Weissenhorn et al.

(10) Patent No.: US 7,262,270 B2
(45) Date of Patent: Aug. 28, 2007

(54) FUSION PROTEIN CONSTRUCT AND METHOD FOR INDUCING HIV-SPECIFIC SERUM IGG AND SECRETORY IGA ANTIBODIES IN-VIVO

(75) Inventors: Winfried Weissenhorn, Grenoble (FR); Don Wiley, deceased, late of Cambridge, MA (US); by David Prashker, legal representative, Magnolia, MA (US); Nicholas Mantis, Williamstown, MA (US); Marian R. Neutra, Sherborn, MA (US); Pamela Kozlowski, West Roxbury, MA (US)

(73) Assignee: Children's Medical Center Corporation, Boston, MA (US)

( * ) Notice: Subject to any disclaimer, the term of this patent is extended or adjusted under 35 U.S.C. 154(b) by 276 days.

(21) Appl. No.: 10/655,667

(22) Filed: Sep. 5, 2003

(65) Prior Publication Data
US 2004/0096458 A1 May 20, 2004

Related U.S. Application Data

(63) Continuation of application No. PCT/US02/09353, filed on Mar. 27, 2002.

(51) Int. Cl.
*A61K 38/00* (2006.01)
*A61K 39/00* (2006.01)
*A61K 39/12* (2006.01)
*C07K 1/00* (2006.01)

(52) U.S. Cl. ............... 530/324; 530/350; 530/826; 424/185.1; 424/188.1; 424/192.1; 424/202.1; 424/204.1

(58) Field of Classification Search ........... 530/324, 530/350, 826; 424/185.1, 188.1, 189.1, 192.1, 424/202.1, 204.1
See application file for complete search history.

(56) References Cited

OTHER PUBLICATIONS

Abaza et al, "Effects of amino acid substitutions outside an antigenic site on protein binding to monoclonal antibodies of predetermined specificity obtained by peptide immunization", Journal of Protein Chemistry, vol. 11, No. 5 (1992), pp. 433-444.*
Cruse et al. Illustrated Dictionary of Immunology (Boca Raton, FL, CRC Press, Inc., 1995), p. 309. QR180.4.C78.*
Paul, Fundamental Immunology, (Philadelphia & New York, Lippincott-Raven Publishers, 1993), pp. 250 and 1311-1312. QR181.F84.*
Cohen et al. "Pronounced acute immunosuppression in vivo mediated by HIV Tat challenge", Proceedings of the National Academy of Sciences of the United States of America, vol. 96, Issue 19(Sep. 14, 1999), pp. 10842-10847.*
Weissenhorn et al. "Assembly of a rod-shaped chimera of a trimeric GCN4 zipper and the HIV-1 gp41 ectodomain expressed in *Escherichia coli*" Proceedings of the National Academy of Sciences. USA vol. 94, (Jun. 1997) pp. 6065-6069.*
Harbury et al., SCIENCE * vol. 262 * Nov. 26, 1993; p. 1401-1407.*

* cited by examiner

*Primary Examiner*—Bruce R. Campell
*Assistant Examiner*—Stuart W. Snyder
(74) *Attorney, Agent, or Firm*—David Prashker

(57) ABSTRACT

The present invention provides a fusion protein construct (gp41HA) consisting of the ectodomain of the HIV-1$_{IIIB}$ envelope glycoprotein gp41 fused to a fragment of the influenza virus HA2 hemagglutinin protein. Immunization in-vivo via an intraperitoneal prime followed by intranasal or intragastric boosts with gp41HA induces high concentrations of serum IgG antibodies and fecal IgA antibodies that reacted with gp41 in HIV-1$_{IIIB}$ viral lysate and are cross-reactive with gp41 in HIV-1$_{MN}$ lysate. Followup analyses by indirect immunofluorescence showed that both serum IgG and fecal IgA recognized human peripheral blood mononuclear cells infected with either syncytium-inducing (SI) or non-syncytium-inducing (NSI) North American HIV-1 field isolates, but not uninfected cells.

15 Claims, 6 Drawing Sheets

Fig. 5A 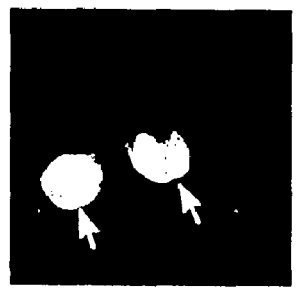  Fig. 5B
Fig. 5C   Fig. 5D
Fig. 5E 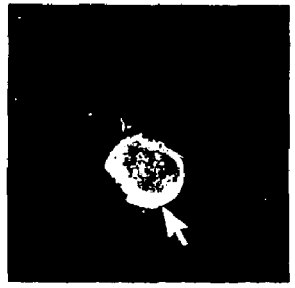  Fig. 5F Fig. 6A 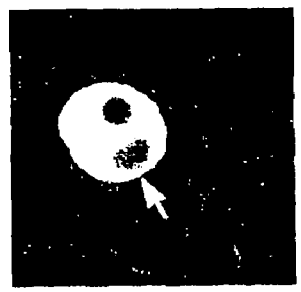  Fig. 6B
Fig. 6C   Fig. 6D

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 1:

```
Gln Ala Arg Gln Leu Leu Ser Gly Ile Val Gln Gln Gln Asn Asn Leu Leu
 1               5                  10                  15

Arg Ala Ile Glu Ala Gln Gln His Leu Leu Gln Leu Thr Val Trp Gly Ile
             20                  25                  30

Lys Gln Leu Gln Ala Arg Ile Leu Ala Val Glu Arg Tyr Leu Lys Asp Gln
 35                  40                  45                  50

Gln Leu Leu Gly Ile Trp Gly Cys Ser Gly Lys Leu Ile Cys Thr Thr Ala
                 55                  60                  65

Val Pro Trp Asn Ala Ser Trp Ser Asn Lys Ser Leu Glu Gln Ile Trp Asn
 70                  75                  80                  85

His Thr Thr Trp Met Glu Trp Asp Arg Glu Ile Asn Asn Tyr Thr Ser Leu
                 90                  95                  100

Ile His Ser Leu Ile Glu Glu Ser Gln Asn Gln Gln Glu Lys Asn Glu Gln
            105                 110                 115

Glu Leu Leu Glu Leu Asp Lys Trp Ala Ser Leu Trp Asn Trp Phe Asn Ile
120                 125                 130                 135
```

-continued

```
Thr Asn Trp (2) INFORMATION FOR SEQ ID NO: 2:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

Ala Ile Asp Gln Ile Asn Gly Lys Leu Asn Arg Val Ile Glu Lys Thr Asn
1               5                   10                  15

Glu Lys Phe His Gln Ile Glu Lys Glu Phe Ser Glu Val Glu Gly Arg Ile
            20                  25                  30

Gln Asp Leu Glu Lys Tyr Val Glu Asp Thr Lys
35                  40                  45

(2) INFORMATION FOR SEQ ID NO: 3:

(i) SEQUENCE CHARACTERISTICS:
        (A) LENGTH: 185 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Met Gln Ala Arg Gln Leu Leu Ser Gly Ile Val Gln Gln Gln Asn Asn
1               5                   10                  15

Leu Leu Arg Ala Ile Glu Ala Gln Gln His Leu Leu Gln Leu Thr Val
            20                  25                  30

Trp Gly Ile Lys Gln Leu Gln Ala Arg Ile Leu Ala Val Glu Arg Tyr
            35                  40                  45

Leu Lys Asp Gln Gln Leu Leu Gly Ile Trp Gly Ser Ser Gly Lys Leu
50                  55                  60

Ile Ser Thr Thr Ala Val Pro Trp Asn Ala Ser Trp Ser Asn Lys Ser
65                  70                  75                  80

Leu Glu Gln Ile Trp Asn His Thr Thr Trp Met Glu Trp Asp Arg Glu
                85                  90                  95

Ile Asn Asn Tyr Thr Ser Leu Ile His Ser Leu Ile Glu Glu Ser Gln
                100                 105                 110

Asn Gln Gln Glu Lys Asn Glu Gln Glu Leu Leu Glu Leu Asp Lys Trp
            115                 120                 125

Ala Ser Leu Trp Asn Trp Phe Asn Ile Leu Asp Gly Ala Ile Asp Gln
130                 135                 140

Ile Asn Gly Lys Leu Asn Arg Val Ile Glu Lys Thr Asn Glu Lys Phe
145                 150                 155                 160

His Gln Ile Glu Lys Glu Phe Ser Glu Val Glu Gly Arg Ile Gln Asp
                165                 170                 175

Leu Glu Lys Tyr Val Glu Asp Thr Lys
            180                 185

(2) INFORMATION FOR SEQ ID NO: 4:

(i) SEQUENCE CHARACTERISTICS:
        (A) LENGTH: 558 base pairs
```

-continued

```
        (B)  TYPE: nucleic acid
        (C)  STRANDEDNESS: single
        (D)  TOPOLOGY: linear (ii) MOLECULE TYPE: DNA (xi) SEQUENCE DESCRIPTION: SEQ ID NO: 4:

ATGCAAGCAC GCCAATTATT GTCTGGTATA GTGCAGCAGC AGAACAATTT GCTGAGGGCT      60

ATTGAGGCGC AACAGCATCT GTTGCAACTC ACAGTCTGGG GCATCAAGCA GCTCCAGGCA     120

AGAATCCTGG CTGTGGAAAG ATACCTAAAG GATCAACAGC TCCTGGGGAT TTGGGGTAGC     180

TCTGGTAAAC TGATCAGCAC CACTGCTGTG CCTTGGAATG CTAGTTGGAG TAATAAATCT     240

CTGGAACAGA TTTGGAATCA CACGACCTGG ATGGAGTGGG ACAGAGAAAT TAACAATTAC     300

ACAAGCTTAA TACACTCCTT AATTGAAGAA TCGCAAAACC AGCAAGAAAA GAATGAACAA     360

GAATTATTGG AATTAGATAA ATGGGCAAGT TTGTGGAATT GGTTTAACAT TCTAGATGGA     420

GCCATCGACC AAATCATCAA TGGGAAATTG AACAGGGTAA TCGAGAAGAC GAACGAGAAA     480

TTCCATCAAA TCGAAAAGGA ATTCTCAGAA GTAGAAGGGA GAATTCAGGA CCTCGAGAAA     540

TACGTTGAAG ACACTAAA                                                  558

(2) INFORMATION FOR SEQ ID NO: 5:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Glu Leu Asp Lys Trp
1               5
```

FUSION PROTEIN CONSTRUCT AND METHOD FOR INDUCING HIV-SPECIFIC SERUM IGG AND SECRETORY IGA ANTIBODIES IN-VIVO

This application is a continuation of international application number PCT/US02/09353, filed 27 Mar. 2002, now pending.

RESEARCH SUPPORT

The research for the present invention was supported in part by NIH grants GM39589, HD-17557, and AI-34757. The U.S. government has certain rights in the invention.

FIELD OF THE INVENTION

The present invention is concerned generally with humoral antibodies specific against epitopes of human immunodeficiency virus (HIV). It is particularly directed to the synthesis and use of gp41 fusion protein constructs as immunogens and vaccines effective for inducing HIV-specific serum IgG and secretory IgA antibodies in vivo.

BACKGROUND OF THE INVENTION

There is presently a worldwide demand for an efficacious vaccine that reduces the risk of sexual transmission of the human immunodeficiency virus type 1 (HIV-1) across cervicovaginal and rectal mucosae. In the female genital tract, it is thought that HIV-1 is initially "sampled" by motile intraepithelial or subepithelial dendritic cells and may initially infect mucosal T cells [Hussain et al., *Immunology* 85: 474-484 (9995); Parr et al., *Biol. Reprod.* 45: 261-265 (1991); Pope et al., *J. Infect. Dis.* 179: S427-S430 (1999); Spira et al., *J. Exp. Med.* 183: 215-225 (1996)]. In the rectum HIV-1 may enter via damaged epithelium or may cross an intact epithelial barrier via colonocytes or via specialized antigen transporting epithelial cells known as M cells [Amerongen et al., *J. Acq. Immun Def. Synd.* 4: 760-765 (1991); Bomsel, M., *Nature Med.* 3: 42-47 (1997)]. Once within the mucosa HIV-1 replicates in resident CD4+ T lymphocytes and/or macrophages and may be carried by these cells, as well as dendritic cells, to draining lymphoid organs within days after initial exposure [Ignatus et al., *J. Med. Pathol.* 27: 121-128 (1998); Miller et al., *J. Med Primatol.* 21: 64-68 (1992); Pope et al., *Cell* 78: 389-398 (1994); Stahl-Henning et al., *Science* 285: 1261-1265 (1999)].

Humoral Immunity:

Humoral immunity plays a critical role in preventing and/or modulating infection with the primate lentiviruses, including HIV, simian immunodeficiency virus (SIV), and the HIV-SIV chimeric virus SHIV [Moore & Burton, *Nature Medicine* 5: 142-144 (1999)]. For example, experiments in chimpanzees demonstrated that immunoglobulin (Ig) from the serum of HIV-infected individuals (HIVIG), monoclonal Ab (mAb), chimeric mAb, and anti-CD4-immunoglobulin IgG can all prevent infection with HIV; and that a human mAb to gp41 can significantly delay signs of infection [Prince et al., *AIDS Res. Hum. Retrovir.* 7: 971-973 (1991); Emini et al., *Nature* 355: 728-730 (1992); Emini et al., *J. Virol.* 64: 3674-3678 (1990); Conley et al., *J. Virol.* 70: 6751-6758 (1996)].

These studies of protection of chimpanzees by passive immunization suggest that the best correlates of immunoprophylaxis within in vivo studies are effective virus neutralizing activity in vitro and a slow Ab dissociation rate constant [Van Cott et al., *J. Immunol.* 153: 449-459 (1994)]. Similarly, most studies in mice reconstituted with human peripheral blood mononuclear cells exhibiting severe combined immunodeficiency syndrome (hu-PBL-SCID) have also demonstrated that pre- and postexposure protection against HIV infection can be mediated by murine mAb, human mAb, and mouse-human chimeric mAb [Safrit et al., *AIDS* 7: 17-21 (1992); Gauduin et al., *J. Infect. Dis.* 171: 1203-1209 (1995); Parren et al., *AIDS* 9: F1-F6 (1995); Gauduin et al., *Nature Med.* 3: 1389-1390 (1997)]. All of these studies suggest that Ab of appropriate specificities can prevent HIV and SIV infection with cell-free virions and of slowing viral replication and disease progression.

Active Immunization Studies:

Vaccine studies in primate models have increased our understanding of the interplay of viral replication and host immunity. Conjectured for a number of years, and now documented in several primate studies, is the observation that infection with live-attenuated viral vaccines induces strong cellular and humoral immunity, including neutralizing Ab effective against the macaque-grown challenge virus stocks, which can be considered primary isolates in this system.

The induction of these humoral responses is dependent upon a threshold of replication of the attenuated virus during primary viremia [Ruprecht et al., *AIDS* 10: S33-S40 (1996)]. Below this threshold, immune responses are weak and full protection is not seen except with very weak virus challenges; above the threshold, strong host immunity is observed in most animals and protection from infection with highly pathogenic SIV challenges ensues. These data and those obtained in vaccine studies with live-attenuated SIV, summarized by Table A below, support the notion that the level of attenuated virus replication during primary infection predicts whether the immune response is sufficient to block infection upon subsequent challenge with wild type virus.

Unfortunately, several examples of pathogenic effects from highly attenuated live viral vaccines were documented in five laboratories during the 1998 year, as summarized in a recent editorial [Cohen, J., *Science* 278: 24-25 (1997)]. Thus, it remains the difficult goal of vaccinologists either: (1) to construct live-attenuated viruses that are both effective and safe, or (2) to mimic the presentation of viral proteins observed in infection with recombinant antigens or with replicating or non-replicating vectors carrying appropriate genes or antigens.

TABLE A*

Summary of representative HIV/SIV vaccine approaches in primate models

| Host/viral pair | Relative pathogenicity | 'Sterilizing' immunity (partial protection or reduction in viral load) | Challenge virus | Neutralizing antibody induced | Correlate of protection |
|---|---|---|---|---|---|
| Chimpanzee/ HIV-1 | Low | gp120 subunit [Refs. 1 and 2] | $HIV_{SF2}$; $HIV_{IIIB}$ | + | Yes |
| | | Vaccinia gp160 + V3 peptide [Ref. 3] | $HIV_{IIIB}$ | + | Yes |
| | | DNA encoding gp160 [Ref. 4] | $HIV_{SF2}$ | +/− | Yes |
| | | Adenovirus gp160 + gp120 subunit [Refs. 5 and 6] | $HIV_{SF2}$ | +, 1° | Yes |
| | | Canarypox-gag-prot-env [Ref. 7] | $HIV_{IIIB}$ (cell associated) | +/− | Yes |
| Macaque/ SHIV | Low | Canarypox-gag-prot/env +/− subunit boost [Ref. 7] | $HIV_{DH12}$ | − | No |
| | | (DNA encoding HIV gp120) [Ref. 8] | $SHIV_{-HXB2}$ | + | Yes |
| | | (gp160 subunit) [Ref. 9] | $SHIV_{-HXB2}$ | + | Yes |
| | | (Vaccinia-gag-pol-env + gag-pol VLP, gp160 subunit) [Ref. 9] | $SHIV_{-HXB2}$ | + | Yes |
| | | gp120 subunit in ISCOMS + V2/V3 peptide boost [Ref. 10] | SHIV-primary | + | Yes |
| | | Live-attenuated SIV; high replicative capacity [Refs. 11, 12 and 13] | $SHIV_{-HXB2}$/ $SHIV_{-DH12}$ | − | No |
| | | Vaccinia-gp160 + gp160 subunit [Ref. 9] | $SHIV_{-HXB2}$ | + | Yes |
| | | DNA encoding gp160t + gp120 subunit [Ref. 14] | $SHIV_{-HXB2}$ | + | Yes |
| Macaque/ SIVmneE11s or SIVmne (uncloned) | Moderate | (gp160 subunit) [Ref. 15] | $SIV_{mneE11S}$ | + | No |
| | | (Vaccinia-gp160 + gp160 subunit) [Ref. 15] | $SIV_{mneE11S}$; $SIV_{mne}$ | + | No |
| | | (Vaccinia-gag-pol + Gag-Pol VLP) [Ref. 15] | $SIV_{mneE11S}$ | + | No |
| | | Vaccinia-gag-pol-env − Gag-Pol-Env VLP [Ref. 15] | $SIV_{mneE11S}$ | + | No |
| | | Vaccinia-gag-pol; env + Gag-Pol VLP + gp160 subunit [Ref. 15] | $SIV_{mne}$ | + | No |
| Macaque/ SIVsmE660 or $SIV_{mac251}$ or $SIV_{239}$ | High | (Vaccinia-gp160 and gp160 subunit) $SIV_{mac251}$ [Ref. 15-18] | $SIV_{smE660}$; $SIV_{mac239}$ | + | No |
| | | (Live-attenuated SIV; low replicative capacity) [Ref. 19] | $SIV_{mac251}$ (ivag) | + | No |
| | | (Live-attenuated high-replicative capacity SHIV) [Refs. 12 and 20] | $SIV_{mac239}$ (ivag); $SIV_{sm}$ (IR) | − | No |
| | | (Adenovirus-gp120 + gp120 subunit) [Ref. 21] | $SIV_{mac251}$ (ivag) | + | Yes |
| | | Live-attenuated SIV; high replicative capacity [Refs. 22-25] | $SIV_{mac251}$ $SIV_{smmPRj}6.6$ | +, 1° | Yes |

Yes, neutralization against homologous laboratory isolate; SIV, simian immunodeficiency virus; SHIV, simian-human immunodeficiency virus; 1°, includes neutralization of primary isolates.
*Reproduced from Haigwood N. L. + S. Zolla-Pazner, AIDS 12: S121-S132 (1998), p. S127.
References
Ref. 1: El-Amad et al., AIDS 9: 1313-1322 (1995).
Ref. 2: Berman et al., Nature 345: 622-625 (1990).
Ref. 3: Girard et al., Proc. Natl. Acad. Sci. USA 88: 542-546 (1991).
Ref. 4: Boyer et al., Nature Med. 3: 526-532 (1997).
Ref. 5: Lubeck et al., Nature Med. 3: 651-658 (1997).
Ref. 6: Zolla-Pazner et al., J. Virol. 72: 1052-1059 (1998).
Ref. 7: Girard et al., Virology 232: 98-104 (1997).
Ref. 8: Robinson, H. L. AIDS 11: S109-S119 (1997).
Ref. 9: Hu et al., 9th Annual Meeting of the National Cooperative Vaccine Development Group for AIDS, Bethesda, MD, 1997, Abstract No. 69.
Ref. 10: Heeney et al., 15th Annual Symposium on Nonhuman Primate Models for AIDS, Seattle, WA, 1997, Abstract No. 5.
Ref. 11: Dunn et al., AIDS Res. Hum. Retrovir. 13: 913-922 (1997).
Ref. 12: Miller et al., J. Virol. 71: 1911-1921 (1997).
Ref. 13: Shibata et al., J. Virol. 71: 8141-8148 (1997).
Ref. 14: Letvin et al., Proc. Natl. Acad. Sci. USA 94: 9378-9383 (1997).
Ref. 15: Hu et al., Immun. Lett. 51: 115-119 (1996).
Ref. 16: Hirsch et al., J. Virol. 70: 3741-3752 (1996).
Ref. 17: Ahmad et al., AIDS Res. Hum. Retrovir. 10: 195-204 (1994).
Ref. 18: Daniel et al., AIDS Res. Hum. Retrovir. 10: 839-851 (1994).
Ref. 19: Marthas et al., J. Virol. 64: 3694-3700 (1990).
Ref. 20: Quesda-Rolauder et al., AIDS Res. Hum. Retrovir. 12: 993-999 (1996).
Ref. 21: Buge et al., J. Virol. 71: 8531-8541 (1997).
Ref. 22: Wyand et al., J. Virol. 70: 3724-3733 (1996).
Ref. 23: Lewis et al., 15th Annual Symposium on Nonhuman Primate Models for AIDS, Seattle, WA, 1997, Abstract No. 1.
Ref. 24: Wyand et al., Nature Med. 3: 32-36 (1997).
Ref. 25: Daniel et al., Science 228: 1201-1204 (1992).

'Prime/Boost' and Subunit Vaccines Tested by Challenge with SHIV and SIV:

It has been shown that immunization with HIV-1$_{LA1}$ gp160 vaccines, in a recombinant vaccinia virus priming and subunit boosting regimen, protected macaques against SIV HXBc2 challenge [Haigwood, N. L. and S. Zolla-Pazner, AIDS 12: S121-S132 (1998)]. Using the same challenge model, it was found subsequently that subunits alone were not protective (gp120; none out of three protected) or partially protective (gp160; two out of four protected). Complete protection was observed in all six macaques that received vaccinia virus-expressing HIV-1 gp160 and boosts of either gp120 (three out of three protected) or gp160 (three out of three protected). More complex immunogens including Env-bearing pseudovirion particles were partially effective in providing protection against SHIV challenge (three out of five protected). These data underline the importance of providing sufficient Env protein in vaccine preparations.

The HIV Envelope Glycoprotein:

An overview of the scientific reports shows that the envelope glycoprotein (env) of human immunodeficiency virus-1 (HIV-1) is synthesized as a precursor molecule gp160 and subsequently processed into its subunits gp120 and gp41. Gp120 is non-covalently associated with gp41 and contains the binding sites for CD4 molecules, i.e., the cellular receptors of HIV-1, and the chemokine receptors such as CCR4 and CXCR5. The gp41 subunit is anchored in the membrane and has a non-polar fusion peptide at its N-terminus. The gp120-gp41 molecule forms oligomers on the infected cell surface and on virions. Strong evidence for trimeric oligomers states has been reported at length in the published scientific literature.

The binding of gp120 to CD4 is thought to result in activation of the membrane fusion activity of gp41, leading to entry of the viral nucleocapsid into a cell. Evidence for a conformational change in the viral glycoprotein upon binding CD4 includes alterations in antibody reactivity, increased protease sensitivity and the dissociation of gp120.

Recent publications which factually support this summary overview include the following: Allan et al., *Science* 228: 1091-1094 (1985); Veronese et al., *Science* 229: 1402-1405 (1985); Dagleish et al., *Nature* 312: 763-767 (1984); Klatzman et al., *Nature* 312: 767-768 (1984); Madden et al., *Cell* 47: 333-348 (1986); Bosch et al., *Science* 244: 694-697 (1989); Kowalski et al., *Science* 237: 1351-1355 (1987); Gelderblom et al., *Virology* 156: 171-176 (1987); Pinter et al., *Virology* 83: 417-422 (1977); Schawaller et al., *Virology* 172: 367-369 (1989); Earl et al., *J. Virol.* 68: 3015-3026 (1994); Weiss et al., *J. Virol.* 64: 5674-5677 (1990); and Sattentau Q. and J. P. Moore, *J. Exp. Med.* 174: 407-415 (1991); Weissenhorn et al., *PNAS* 94: 6065-6069 (1997); Weissenhorn et al., *EMBO J.* 15: 1507-1514 (1997); Weissenhorn et al., *Molecular Membrane Biologs* 16: 3-9 (1998); and Weissenhorn et al., *Nature* 387: 426-430 (1997).

Antigen Structures which Induce Ab Responses:

Since the form of immunogen affects the type and specificity of the immune response, the nature of the immunogens found in natural infection that elicit Ab becomes a pivotal issue which impacts on vaccine design. Anti-HIV envelope polyclonal and monoclonal antibody preparations react with HIV-infected cells, implying that infected cells express envelope antigens that serve to both induce Ab and act as their targets. Thus, HIV+ sera and mAb to gp41 and the V3 and C5 regions of gp120 have been shown to stain cells infected with primary isolates and to mediate neutralization and/or Ab-dependent cell-mediated cytolysis (ADCC) [Zolla-Pazner et al., *J. Virol.* 69: 3807-3815 (1995); Tyler et al., *J. Immunol.* 145: 3276-3282 (1990); Alsmadi et al., *J. Virol.* 71: 925-933 (1997); Bauir et al., *J. Immunol.* 157: 2168-2173 (1996). This demonstrates that infected cells express virus-derived antigens. Oligomeric envelope proteins also are immunogenic.

As summarized in a recent paper [Haigwood, N. L. and S. Zolla-Pazner, *AIDS* 12: S121-S132 (1998)], while oligomer-specific mAb have only been described in immunized mice and rabbits, several human mAb have been described which show better reactivity with polymeric than with monomeric HIV envelope molecules. Amongst the first of these were human mAb to gp41 which preferentially react with oligomeric forms of gp41 on Western blot [Zolla-Pazner et al., *N. Engl. J. Med.* 320: 1280-1281 (1989); Pinter et al., *J. Virol.* 63: 2674-2679 (1989)]. Later studies suggested that mAb IgG1b12, specific for the CD4 binding domain preferentially binds to structures exposed on oligomeric envelope protein [Fouts et al., *J. Virol.* 71: 2779-2785 (1997)]; and mAb 2F5, specific for an epitope near the transmembrane region of gp41, binds to the oligomeric structure of gp41 in the virion envelope, resulting in neutralization [Muster et al., *J. Virol.* 68: 4031-4034 (1994)]. That all of these mAb also recognize structures on the monomeric forms of gp120 or gp41 is shown by the fact that the hybridoma cell lines producing these mAb were each selected using monomeric forms of these envelope glycoproteins.

Immune Responses to gp41:

Recently there has been a renewed interest in the immune response to gp41. The potential importance of Ab to gp41 is well demonstrated by the human mAb 2F5 which is specific for the ELDKW [SEQ ID NO:5]epitope near the transmembrane domain of gp41 and has broad neutralizing activity for laboratory-adapted strains and primary isolates of HIV [Muster et al., *J. Virol.* 68: 4031-40343 (1994)]. Other anti-gp41 mAb also have been shown to neutralize both laboratory-adapted and primary isolates of HIV [Hioe et al., *Int. Immunol.* 9: 1281-1290 (1997); Cotropia et al., *AIDS Hum. Retrovir.* 12: 221-232 (1996)]; and it was recently suggested that Ab to gp41 epitopes in the serum of HIV-infected individuals may play an important role in virus neutralization [McKeating et al., *Virology* 220: 450-460 (1996)].

Additional interest comes from research on the structure of gp41 and its role in infectivity. Thus, gp41, which mediates fusion between viral and cellular membranes, has been shown to consist of a rod-like molecule with a high alpha-helical content [Weissenhorn et al., *EMBO J.* 15: 1507-1514 (1996)]; and the structure of the fusogenic form appears to be composed of a six-helical bundle of two regions of the gp41 molecule. The core of the gp41 structure forms an extended, triple stranded coiled coil derived from a predicted leucine zipper domain approximately 30 residues from the N-terminal fusion peptide. A C-terminal a-helix packs in the reverse direction against the outside of the coiled coil following the groove between two core helices [Weissenhorn et al., *Nature* 387: 426-430 (1997); Chan et al., *Cell* 89: 263-273 (1997)]. The soluble forms of gp41 visualized by two crystal structures contain gp41 residues 30 to 79 and 113 to 153 [Weissenhorn et al., *Nature* 387: 426-430 (1997)] and a smaller construct contains residues 35 to 70 and 117 to 150 [Chan et al., *Cell* 89: 263-273 (1997)]. The conformational and linear epitopes exposed on gp41 appear to be different in gp41/gp120 nonfusogenic configuration and in the fusion active conformation [Sattentau et al., 1995; Weissenhorn et al., *EMBO J.* 15: 1507-1514 (1996)].

It has been suggested that the conformational structure of gp41 provides the fusion-active capability for gp41. A general model was presented where the complex of gp120/gp41 undergoes major conformational changes after interaction with cellular receptors CD4 and chemokine receptors [Berger et al., *Annu Rev Immunol* 17: 886-900 (1999)]. The conformational changes occurring in gp41 are thought to open up intermediary conformational states and the complete refolding of the molecule results in the helical hairpin structure observed by crystallography. This process is thought to pull two membranes into close proximity and induce fusion of viral and cellular membranes [see FIG. 3 in Weissenhorn et al., *Nature* 387: 426-430 (1970). It is conceivable that monoclonal antibodies that either block the formation of the helical hairpin, like gp41 specific peptides [Kilby et al., *Nat. Med.* 4: 1302-1307], or block the aggregation of gp41 helical hairpin structures (a number of trimers are necessary at the site of fusion [Danilei et al., *J. Cell Biol.* 133: 559-569 (1996)]) at the site of fusion may inhibit membrane fusion and thus infection.

HIV Envelope Glycoprotein Variants, Synthetic Chimeras, and gp41 Structure:

In recognition of the fact that the HIV envelope subunit gp41 plays such a critical role in viral entry by initiating fusion of viral and cellular membranes, Weissenhorn and colleagues have synthesized new construct variants of the ectodomain of HIV-1 and the env gp41 subunit in particular. Thus it has been shown that the env subunit gp41 forms a slightly soluble, (alpha)-helical, rod-like oligomer in the absence of gp120 and the N-terminal fusion peptide [Weissenhorn et al., *EMBO J.* 15: 1507-1514 (1996)]; and also that a rod shaped chimera of a trimeric GCNA zipper and the HIV-1 gp41 ectodomain can be synthesized and expressed in *E. coli* and solubilized by proteolysis [Weissenhorn et al., *Proc. Natl. Acad. Sci. USA* 94: 6065-6069 (1997)]; and that the atomic structure of the ectodomain from HIV gp41 is an extended, triple stranded alpha-helical coil with the N-terminus at its tip [Weissenhorn et al., *Nature* 387: 426-430 (1997)]. The core of the molecule forms an extended, triple-stranded alpha-helical coiled coil with the N-terminus at its tip. A C-terminal alpha-helix packs in the reverse direction against the outside of the coiled coil following the groove between two core helices. This arrangement places the N-terminal fusion peptide and the C-terminal transmembrane region at the same end of the rod-shaped molecule [Weissenhorn et al., 1997].

These reported investigations and published papers centered in particular upon finding new synthetic chimeras which might substantially increase the solubility of gp41— and thus possibly increase the number of epitopes exposed as well as the potential antigenicity of the gp41 amino acid sequences. As noted in these recently published papers, the crystal structures were derived from different sources. Core fragments of gp41 were either assembled from synthetic peptides [Chan et al., 1997], or expressed in *E. coli* and solubilized with a trimeric GCN4 zipper fused to the predicted N-terminal coiled coil and trimmed by proteolysis [Weissenhorn et al., 1997]. Alternatively, *E. coli* expressed N-terminal and C-terminal helical regions were connected by a synthetic linker [Tan et al., 1997].

All three gp41 structures constructed in this manner (as described in the published papers) are missing the N-terminal region containing the hydrophobic fusion peptide and the loop that connects a N-terminal core helix with a C-terminal helix. The HIV gp41/GCN4 chimera is missing 39 linker residues, which would contain a short disulphide linked loop and two carbohydrate sites [Weissenhorn et al., *Nature* (1997)]. Although the disulphide linked loop C-terminal of the coiled coil region is characteristic for all retroviral and filoviral fusion proteins, its function is not yet known. The disulphide linked loop in HIV might play a role in the change of conformation as determined by differential antibody reactivity [Weissenhorn et al., *EMBO J.* (1996)].

Gp41 sequences of different HIV subtypes show a remarkable conservation for the N-terminal coiled coil as well as for the C-terminal residues that interact with the N-terminal core structure [Weissenhorn et al., *Nature* (1997); Chan et al., *Cell* (1997)]. Indeed, there are only conservative changes within interfaces of two N-terminal helices and one C-terminal helix, and most of the differences are on the outside of the C-terminal helix, exposed to the solvent. This reveals that the C-terminal helix packs into a highly conserved groove along the core coiled coil, which is remarkable considering the sequence variability in HIV [Myers et al., 1995].

In addition, there are several lines of evidence that the gp41 membrane fusion protein exists in two conformations: a native conformation in complex with gp120; and a fusion-conformation. First, receptor binding was shown to increase the exposure of gp41 epitopes [Sattentau and Moore, 1992] as well as to stimulate the dissociation of gp120 from gp41 [Kirsh et al., 1990; Moore et al., 1990; Hart et al., 1991]. Antibodies raised against native gp41 (in complex with gp120) [Earl et al., 1994] showed a differential reactivity with gp41 expressed (without gp120) in insect cells. Some of the antibodies were mapped to the short disulphide linked loop and recognized native gp41 but not the fusion conformation [Weissenhorn et al., 1996].

Second, direct evidence arises from a number of mutagenesis studies, which showed that residue changes especially within the heptad positions of the central coiled coil affect infectivity and membrane fusion, but not processing and cell surface expression of gp41/gp120 complexes [Dubay et al., 1992; Cao et al., 1993; Chen et al., 1993; Chen 1994]. This indicates that these changes are tolerated in the native conformation but not in the fusion conformation.

Third, peptides derived from the gp41 sequence, like DP-107 (part of the N-terminal coiled coil) and DP-178 (C-terminal helix, with an expression towards the transmembrane region), have potent anti-viral activity [Jiang et al., 1992; Wild et al., 1992; 1994; Lawless et al., 1996]. The structure of gp41 confirms the view that these derived peptides expert their effect by interacting with gp41 during the receptor induced conformational change. This is also consistent with the finding that the assembled complex (N- and C-terminal helices) has no anti-viral activity [Lu et al., 1995]. The conformation of gp41, as observed in the crystal structure, shows a temperature dependent denaturation at approximately 80° C. [Blacklow et al., 1995; Lu et al., 1995; Weissenhorn et al., 1996]; which makes it unlikely that the complex comes apart and interacts with individual peptides. Kinetic measurements of receptor-activated conformational changes showed that these changes are initiated within a few minutes and completed after 20 min [Jones et al., 1998]. It is also remarkable that the C-terminal peptide (DP-107) remains active even when added after mixing of the target cells [Munoz-Barroso et al., 1998]. The C-terminal peptide DP-178 does not interact with native gp41, but binds to gp41 after induction of receptor mediated conformational changes, an event which confirms the structural changes in gp41 upon receptor binding [Furuta et al., 1998].

Immunization:

It is generally agreed that multiple immune effectors participate in prevention, containment and clearance of HIV infection. To prevent infection of host target cells, antibodies are required. After the first target cells have been infected with virus, it is important to have cytotoxic T lymphocytes (CTLs) as well as antibodies to reduce cell-to-cell spread and kill infected cells. The exact amounts of specific antibodies or CTLs required for mucosal or systemic protection against HIV are not known. However, it seems clear that an effective HIV vaccine should evoke antibodies that can bind to virus and prevent attachment of virus to target cells, as well as CTLs that can eliminate any cells that become infected.

If virus is transmitted directly into the body as through injection, accidental needle stick or damaged skin or mucosa, then antibodies and CTLs in the bloodstream, both of which can readily enter tissues, are most important for protection. Vaccines that are injected intramuscularly or intradermally are generally most efficient for inducing these immune effectors in the blood. However, a large proportion of HIV infections are the result of mucosal transmission. This most often occurs via the cervical-vaginal mucosa and the rectal mucosa, but may also occur via the oral mucosa and nasopharyngeal mucosa. The extent to which antibodies and CTLs from blood can prevent, contain or clear mucosal infections at a very early stage, before virus has spread systemically, is not yet clear. Mucosal surfaces have an additional immune protection mechanism: transport of antibodies into secretions. Secretory antibodies can provide the first line of defense, preventing contact of viruses with the mucosal surface and thereby preventing entry into the body and target cell infection altogether (see below). Secretory antibodies are generally not induced by systemic immunization. Immunization via mucosal surfaces is usually required to evoke secretory antibodies and local CTLs and antibodies in mucosal tissues. In experimental animals and humans, these effectors are induced most efficiently at the mucosal site where the vaccine was administered [Haneberg et al., *Infect. Immun.* 62: 15-23 (1994); Kozlowski et al., *Infect. Immun.* 65: 1387-1394 (1997)]. In addition, vaccines administered mucosally may induce antibodies in the bloodstream.

The exact composition of an optimal HIV vaccine, or the protocols or routes by which it should be administered, are not yet established. One type of protocol currently being tested is a combination prime-boost approach in which a live vaccine vector (such as fowlpox) carrying HIV genes is given by injection to prime the immune system, followed by booster doses consisting of subunit antigens (usually the HIV envelope proteins gp120 or gp160). The subunit boost appears to be essential for induction of immune responses in serum. As expected, mucosal secretory antibodies have not been detected in animal experiments and human trials using such protocols. Alternative protocols for induction of secretory antibodies are currently being considered. For example, one possibility is administration by injection of a prime consisting of live HIV vaccine vector or DNA encoding HIV antigens, followed by boosts consisting of HIV envelope antigens, administered via a mucosal surface. The exact form or composition of envelope antigens most appropriate for mucosal administration are not yet established.

Secretory IgA Antibodies:

There is mounting epidemiological and experimental evidence that the presence of secretory immunoglobulin A (S-IgA) antibodies directed against the HIV envelope protein gp41 may reduce or prevent sexual transmission of HIV-1 [Lehner et al., *Nature Med.* 2: 767-775 (1996)]. For example, studies in Kenya and Thailand demonstrated a positive correlation in female sex workers between resistance to HIV-1 infection and the presence of anti-gp160 S-IgA antibodies in cervico-vaginal secretions [Beyer et al., *J. Infect. Dis.* 179: 59-67 (1999); Kaul et al., *AIDS* 13: 23-29 (1999)]. A similar correlation was observed in HIV-seronegative women with HIV-seropositive partners in Italy [Mazzoli et al., *Nature Med.* 3: 1250-1257 (1997)]. IgA isolated from secretions of exposed-uninfected women in both Kenya and Italy inhibited transcytosis of HIV across cultured epithelial monolayers in vitro [Devito et al., *J. Immunol.* 165: 5170-5176 (2000)]. However, Beyrer et al. [*J. Inf. Dis.* 179: 59-67 (1999)] found that anti-gp160 IgA antibodies in cervico-vaginal secretions of HIV-resistant sex workers failed to react with gp120, suggesting the antibodies may recognize epitopes located on gp41. Indeed, a recent study has mapped the epitopes recognized by anti-gp160 S-IgA antibodies from cervico-vaginal secretions of exposed-seronegative sex workers to amino acids 65-68 (LQAR) of the gp41 ectodomain [Pastori et al., *J. Biol. Regul. Homeo. Agts.* 14: 15-21 (2000)]. In vitro, anti-gp41 IgA antibodies purified from colostra of HIV-infected women prevented viral transmission across intestinal epithelial cell monolayers [Bomsel et al., *Immunity* 9: 277-287 (1998)].

Thus, an important goal of an effective HIV vaccine strategy should be to induce anti-gp41 antibodies in secretions of uninfected individuals. However, only two reports have examined the mucosal immunogenicity in mice of peptides representing epitopes of gp41 expressed via live recombinant viral vectors [Durrani et al., *J. Immunol. Meth.* 220: 93-103 (1998); Muster et al., *J. Virol.* 69: 6678-6686 (1995)]. Nevertheless, some additional epitopes that might be useful for mucosal protection immunologically are present in the gp41 ectodomain.

The Continuing Problems:

Induction of antigen-specific IgA on mucosal surfaces poses several challenges. First, mucosal delivery of antigens is required because S-IgA antibodies are induced after mucosal but not parenteral immunization [Mestecky et al., *FEMS Imm. Med. Micro.* 27: 351-355 (2000)]. Vaccines taken up at mucosal sites evoke proliferation of IgA-committed, antigen-sensitized lymphoblasts in organized mucosa-associated lymphoid tissue (O-MALT) that eventually seed local and distant mucosal and glandular tissues with IgA-producing plasma cells [Brandtzaeg et al., in Mucosal Immunology, Acad. Press, 1999, pp. 439-468]. Intranasal immunization of humans, for example, can lead to the appearance of antigen-specific IgA in the secretions of the airways, small intestine, rectum, and female genital tract [Bergquist et al., *Infect. Imm.* 65: 2676-2684 (1997); Kozlowski et al., *Immunol. Lett.* 69: 98 [Abst. 23.8] (1999)]. However, one major recognized difficulty in mucosal immunization is that many antigens fail to cross epithelial barriers and gain access to the O-MALT. A second major problem is that large doses of protein antigen are typically required to achieve sufficient sampling by the MALT due to the presence of mucus, proteases and natural clearance mechanisms on mucosal surfaces [McGhee et al., in Mucosal Immunology, Acad. Press, 1999, pp. 741-757]. A third major difficulty is the current absence of identifiable antigens that can be sampled by the MALT after mucosal immunization and evoke anti-gp41 S-IgA antibodies that recognize clinically relevant isolates of HIV-1.

SUMMARY OF THE INVENTION

The present invention has multiple aspects and functional forms. A first aspect of the invention provides a fusion protein construct which is soluble at physiological pH and is useful as an immunogen for the induction of HIV-antigen specific serum IgG and secretory IgA antibodies in vivo, said fusion protein construct comprising:

a first amino acid residue fragment at the N-terminal end of the construct which represents a majority portion of the amino acid sequence for the ectodomain of the HIV envelope glycoprotein gp41; and a second amino acid residue fragment at the COOH-terminal end of the construct which represents a part of the amino acid sequence constituting the influenza virus hemagglutinin protein.

A second aspect of the invention is an immunogen useful in a vaccine for the induction of HIV-antigen specific serum IgG and secretory IgA antibodies in-vivo, said immunogen comprising:
   a fusion protein construct which is soluble at physiological pH and is comprised of:
      a first amino acid residue fragment at the N-terminal end of the construct which represents a majority portion of the amino acid sequence for the ectodomain of the HIV envelope glycoprotein gp41, and
      a second amino acid residue fragment at the COOH-terminal end of the construct which represents a part of the amino acid sequence for the influenza virus hemagglutinin protein; and
   a biocompatible carrier fluid suitable for carrying and delivering a predetermined aliquot of said fusion protein construct to a prechosen site in a living subject.

A third aspect of the invention presents a vaccine for the induction of HIV-antigen specific serum IgG and secretory IgA antibodies in-vivo, said vaccine comprising:
   a fusion protein construct which is soluble at physiological pH and is comprised of:
      a first amino acid residue fragment representing a majority portion of the amino acid sequence for the ectodomain of the HIV envelope glycoprotein gp41, and
      a second amino acid residue fragment representing a part of the amino acid sequence constituting the influenza virus hemagglutinin protein;
   a biocompatible carrier fluid suitable for carrying and delivering a predetermined aliquot of said fusion protein construct to a prechosen site in a living subject; and
   at least one adjuvant composition dispersed in said carrier fluid.

A fourth aspect of the invention is a method of immunization for the induction of HIV-antigen specific serum IgG and secretory IgA antibodies in-vivo, said immunization method comprising the steps of:
   obtaining an immunogen comprising:
      a fusion protein construct which is soluble at physiological pH and is comprised of:
         a first amino acid residue fragment at the N-terminal end of the construct which represents a majority portion of the amino acid sequence for the ectodomain of the HIV envelope glycoprotein gp41, and
         a second amino acid residue fragment at the COOH-terminal end of the construct which represents a part of the amino acid sequence constituting the influenza virus hemagglutinin protein, and
      a biocompatible carrier fluid suitable for carrying and delivering a predetermined aliquot of said fusion protein construct to a prechosen anatomic site in the living subject;
   systemically administering an aliquot of said immunogen on at least one occasion to the body of the living subject as a primary immunization; and
   mucosally administering an aliquot of said immunogen on at least one occasion to a prechosen mucosal tissue site in the body of the living subject as a secondary immunization.

BRIEF DESCRIPTION OF THE FIGURES

The present invention may be more easily understood and better appreciated when taken in conjunction with the accompanying drawing, in which:
FIGS. 5A-5F are photographs showing immunofluorescent reactions which empirically demonstrate that serum IgG and fecal IgA antibodies from immunized mice react with PBMCs infected with an HIV-1 NSI primary isolate;
and
FIGS. 6A-6D are photographs showing immunofluorescent reactions which empirically demonstrate that fecal IgA antibodies from immunized mice react with PBMCs infected with an HIV-1 SI primary isolate.

DETAILED DESCRIPTION OF THE INVENTION

Figure 1:
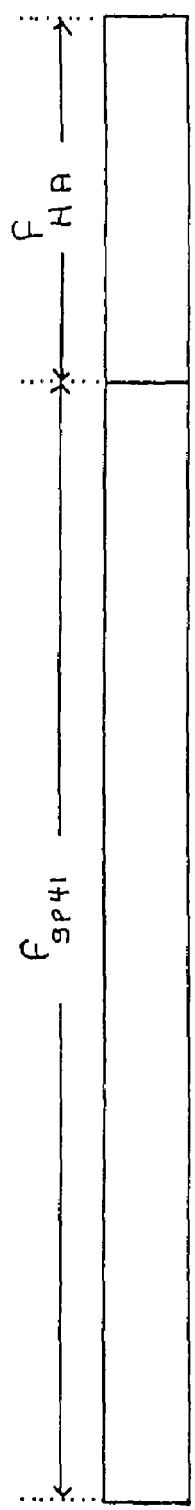
FIG. 1 is a simplified illustration of the fusion protein construct comprising part of the present invention.

The present invention, in its most essential and fundamental form, is a unique fusion protein construct which is prepared for in-vivo use both as an immunogen and as a vaccine; and is effective for inducing a range of specific anti-HIV systemic IgG antibodies and secretory IgA antibodies within the body of the living recipient. An efficacious methodology for the immunization of a living subject using this fusion protein construct as an immunogen and vaccine such that both systemic IgG antibodies and secretory IgA antibodies specific against at least one epitope of human immunodeficiency virus (HIV) are raised in-vivo is also an integral part of the present invention. Accordingly, the present invention provides a number of different unique benefits and major advantages, some of which include the following:

1. The fusion protein construct comprising a part of the invention is a composition constituted of two different amino acid sequence fragments joined linearly in tandem. If desired, the entire fusion protein construct may be synthesized chemically using long-established organic compound synthesis techniques as a complete molecule by joining individual polypeptide fragments together in fixed sequence. It is preferred, however, that the fusion protein construct be a recombinant protein molecule expressed by a genetically modified host cell (such as *E. coli*) cultured in-vitro, which intracellularly carries an introduced expression vector bearing specified recombinant DNA sequences encoding the entirety of the amino acids residues in proper sequence. The manner in which the fusion protein construct is generated is thus merely a question of personal choice and/or convenience.

2. The fusion protein construct is an integrated dipeptide structure, an oligopeptide molecule formed of two distinctly different, polypeptide fragments: a first polypeptide fragment positioned at the N-terminal end which comprises a major portion of the ectodomain of the HIV envelope glycoprotein gp41; and a second polypeptide fragment positioned at the COOH-terminal end which comprises a meaningful part of the influenza virus hemagglutinin protein. Recognizing that a number of different HIV species, subspecies, and strains are currently known to exist—each of which presents a slightly different and individual amino acid residue sequence as its gp41 glycoprotein content and each of which presents a set of both HIV commonly conserved epitopes as well as individually unique epitopes as gp41 antigenic determinants—the fusion protein construct can be formulated and reformulated at will to contain either (or both) a specific HIV epitope, customized construct; or a more generalized, commonly shared and conserved HIV epitope bearing construct. The broader scope of and particular choices for the amino acid residue sequence formulations representing the gp41 peptide fragment of the dipeptide construct allows the manufacturer or intended user to decide in advance what the diversity of epitopes and what the range of antigenic specificities for the IgG and IgA antibodies induced in-vivo shall be.

3. The fusion protein construct when used as an immunogen and/or vaccine can be used, if desired, to induce only IgG antibodies systemically in the recipient host; or, alternatively, can be used to induce both secretory IgA antibodies and systemic IgG antibodies concurrently in the recipient. The mode and manner of administering the fusion protein construct to the recipient will dictate and control the antibody type(s) actually produced in-vivo as the host's humoral immune response.

4. The present invention as a whole is clearly intended for the use and treatment of the *homo sapiens* species, humans, as the primary beneficiaries. However, the fusion protein construct and its medical value as an immunogen and/or vaccine is also available for use with all mammals generally regardless of genus and species. Accordingly, both human medical/clinical applications and veterinary mammalian animal immunizations are envisioned and expected.

5. The fusion protein is expressed within insoluble inclusion bodies in *E. coli* hosts; and it can be refolded in vitro using a physiological buffer. The final yield of refolded protein can be as high as 80 mg from a 1 liter quantity of *E. coli* culture. Successful refolding can be tested by reaction with gp41 specific antibodies and circular dichroism. The addition of the influenza virus HA sequence renders the gp41 polypeptide soluble or causes formation of soluble aggregates. It is envisioned that gp41 sequence fragments from other HIV clades will be also solubilized by this method. A prospective vaccine cocktail will thus potentially include a mixture of gp41 fusion proteins derived from commonly found strains.

6. In the preferred embodiments, the short triple stranded coiled coil sequence derived from the influenza virus hemagglutinin subunit 2 (HA2) is engineered to be a substitute in place of the transmembrane region; and will thus present the gp41 polypeptide in a native way similar to the situation of membrane-anchored gp41 mediated by its own transmembrane region. A similar strategy can be employed to solubilize other HIV specific proteins or unrelated proteins of any nature which form oligopeptides through their transmembrane anchors. The influenza virus HA2 sequence can be therefore seen as a potential soluble transmembrane anchor, which will help to present membrane anchored proteins in a "native-like" conformation in solution. The length of the triple stranded HA2 part can be also varied to potentially achieve better solubilization.

7. A range of different embodiments can be generated as longer-length gp41 variants by including more gp41 residues at the N-terminus as well as at the C-terminus, thus covering close to 100 percent of extracellular gp41 residues. This will improve the immunogenecity of the gp41HA construct, by adding potential additional epitopes.

I. The Parameters of the Fusion Protein Construct

The fusion protein construct is an integrated dipeptide composition and structure, as illustrated in FIG. 1. The fusion protein construct is constituted of two different peptide fragments which are covalently linked together and linearly (axially) joined in tandem sequence to form a unitary polypeptide fusion molecule.

As shown by FIG. 1, the construct is formed of two distinctly different, peptide monomer units: a first peptide fragment which begins at and represents the N-terminal end of the construct and comprises a majority [greater than 50% and preferably 90% or more] portion of the ectodomain for the HIV envelope glycoprotein gp41; and a second peptide fragment located at and representing the COOH-terminal end of the construct and comprises a substantive part (approximately 20%) of the influenza virus hemagglutinin protein.

The Ectodomain of the HIV Envelope Glycoprotein $gp_{41}$

It is recognized that a number of different HIV species, subspecies, and strains are currently known to exist. For example, HIV-1, HIV-2, and HIV-3 species of human immunodeficiency virus have been identified (as reported in the medical and scientific literature). Similarly, a number of different subspecies or clades have been isolated for each major type of HIV species. Thus, the HXB2 strain is merely one example illustrative of the HIV-1 species as a whole. As a point of information, a non-exhaustive listing of strains representative of the HIV-1 family is given by Table 1 below.

Each strain and species of HIV is recognized as having a slightly different and individual amino acid residue sequence formulation for the ectodomain of the envelope glycoprotein gp41. For example, the ectodomain of the HIV-1$_{IIIB}$ envelope glycoprotein gp41 in the HXB2 strain has a specified amino acid residue sequence which is individual and unique in its residue formulation. The HXB2 strain gp41 protein also represents and presents a set of HIV commonly conserved and HXB2 unique amino acid residues in sequence as gp41 antigenic determinants (epitopes). In this manner, depending upon how much of the native ectodomain of the HXB2 (or other strain of HIV-1) envelope glycoprotein gp41 is utilized as the first fragment, the fusion protein construct can be formulated towards either a HXB2 epitope specific, customized construct or towards a more general, commonly conserved HIV-1 epitope bearing construct.

The broader scope of and particular choices for the amino acid residue sequence formulations as the gp41 first peptide fragment of the construct thus allows the maker or intended user to choose in advance what degree of specificity shall exist in the range of antigenic specificities for the IgG and IgA antibodies to be induced in-vivo as the humoral immune response.

TABLE 1

| | HIV-1 species and strains suitable for gp41 fragments |
|---|---|
| A. | HXB2 strain    Fisher et al., Nature (London) 316: 262-265 (1985) |
| B. | All known HIV sequence which are available in the database or referenced by Myers et al., 1995, theoretical biology and biophysics group, Los Alamos, NM. Human retroviruses and AIDS. See also Weissenhorn et al., Nature 387: 426-430. FIG. 1e - sequence comparison of different classes of HIV strains. Each of these publications is expressly incorporated by reference herein. |
| C. | All HIV envelope sequences found at: http://www.ncbi.nlm.nih.gov/retroviruses/using "env" as a search word. All these gp41 sequences can be synthesized and used to make gp41HA fusion proteins. All of these gp41 sequences to be found and identified at this web site are expressly incorporated by reference herein. |

The Influenza Virus Hemagglutinin Protein

It is also recognized that a number of subunits coexist as peptide chains in the influenza virus hemagglutinin protein [Bullough et al., Nature 371: 37 (1994)]. Each of these is distinguishable from the other subunits; and has an individual amino acid residue sequence which is identifiably different from the others. Thus distinct subunits can be isolated from the overall general structure and composition of influenza virus hemagglutinin protein; and subunit 2 of the influenza virus hemagglutin protein represents a unique amino acid sequence formulation. As a point of information, a listing of the different subunits constituting influenza virus hemagglutinin protein is given by Table 2 below.

Subunit 2 of this hemagglutinin protein is the preferred residue sequence formulation and source for the second polypeptide fragment in making the fusion protein construct of the present invention. Here also, because the subunit 2 amino acid sequence represents and presents a set of influenza virus commonly conserved and subunit 2 unique amino acid residues in sequence as gp41 antigenic determinants (epitopes); and because the maker can choose how much of the complete native subunit 2 amino acid residue sequence to employ as the second peptide fragment, the fusion protein construct can be formulated either as a subunit 2 epitope specific, customized construct or as a more general, commonly conserved hemagglutinin protein construct.

The broader scope for and particular choices of the amino acid residue sequence formulations as the influenza virus hemagglutinin protein second fragment of the dipeptide construct thus allows the maker or intended user a second mode of choice to determine in advance what degree of specificity shall exist in the range of antigenic specificities for the IgG and IgA antibodies to be induced in-vivo as the humoral immune response.

TABLE 2

Subunits of influenza virus hemagglutinin protein suitable as a fragment in a fusion protein construct

| Unit/Subunit | Reference(s) |
| --- | --- |
| Subunit 1 | Wiley, D. C. and J. J. Skehel, Annu. Rev. Biochem 56: 365-394 (1987); |
| Subunit 2 | Stegmann, T. and A. Helenius, Virus Fusion Mechanisms, CRC Press, 1993, pp. 89-111 |

See also: Skehel, J. J. and D. C. Wiley, "Receptor binding and membrane fusion in virus entry: The influenza hemagglutinin." Annu. Rev. Biochem. 69: 531-569 (2000) for both subunits of influenza virus HA.
All of these publications are individually incorporated by reference herein.

II. A Preferred Fusion Protein Construct

A preferred integrated fusion protein construct is made based upon the HXYB2 strain of HIV-1 and the subunit 2 of influenza virus hemagglutinin protein. The first peptide fragment of the construct thus desirably has a 138 amino acid residue length and is a modified version of the native amino acid sequence found at residue position nos. 29-167 in the ectodomain of the HIV$_{IIIB}$ envelope glycoprotein gp41 in the HXB2 strain.

The native amino acid residue sequence for positions nos. 29-167 in the gp41 ectodomain is given by Table 3 below. The native sequence contains a cysteine residue at each of position nos. 88 and 94. In the present invention, each of these cysteine residues at position nos. 88 and 94 respectively have been replaced and substituted by serine residues.

In this manner, the disulfide bond existing between these two cysteine residues in the original native gp41 ectodomain sequence between the no. 88 and 94 residues has been eliminated.

A second major point of difference from the native original sequence in the ectodomain of the HXB2 strain original, is that a number of the residues existing in the HXB2 strain at native position nos. 29-167 are glycosylated. In the present invention, none of the amino acid residues employed in the first peptide fragment are glycosylated.

The second peptide fragment in the preferred fusion protein construct of the present invention utilizes the subunit 2 of the influenza virus hemagglutinin protein as the native source for the amino acid residue sequence; and desirably employs only the residues found at position nos. 43-88 respectively. The native amino acid residue sequence at position nos. 43-88 is given by Table 4 below.

TABLE 3

Native gp41 amino acid seq. (nos. 29–167)

Gln-Ala-Arg-Gln-Leu-Leu-Ser-Gly-Ile-Val-Gln-Gln-

Gln-Asn-Asn-Leu-Leu-Arg-Ala-Ile-Glu-Ala-Gln-Gln-

His-Leu-Leu-Gln-Leu-Thr-Val-Trp-Gly-Ile-Lys-Gln-

Leu-Gln-Ala-Arg-Ile-Leu-Ala-Val-Glu-Arg-Tyr-Leu-

Lys-Asp-Gln-Gln-Leu-Leu-Gly-Ile-Trp-Gly-Cys-Ser-

Gly-Lys-Leu-Ile-Cys-Thr-Thr-Ala-Val-Pro-Trp-Asn-

Ala-Ser-Trp-Ser-Asn-Lys-Ser-Leu-Glu-Gln-Ile-Trp-

Asn-His-Thr-Thr-Trp-Met-Glu-Trp-Asp-Arg-Glu-Ile-

Asn-Asn-Tyr-Thr-Ser-Leu-Ile-His-Ser-Leu-Ile-Glu-

Glu-Ser-Gln-Asn-Gln-Gln-Glu-Lys-Asn-Glu-Gln-Glu-

Leu-Leu-Glu-Leu-Asp-Lys-Trp-Ala-Ser-Leu-Trp-Asn-

Trp-Phe-Asn-Ile-Thr-Asn-Trp (SEQ ID NO: 1)

TABLE 4

Native influenza virus hemagglutinin subunit 2, nos. 43–88

Ala-Ile-Asp-Gln-Ile-Asn-Gly-Lys-Leu-Asn-Arg-Val-

Ile-Glu-Lys-Thr-Asn-Glu-Lys-Phe-His-Gln-Ile-Glu-

Lys-Glu-Phe-Ser-Glu-Val-Glu-Gly-Arg-Ile-Gln-Asp-

Leu-Glu-Lys-Tyr-Val-Glu-Asp-Thr-Lys (SEQ ID NO: 2)

Also, the invention prefers to utilize the amino acid residues found at nos. 43-88 of subunit 2 in a non-glycosylated form, rather than the glycosylated residues existing in the native original. The absence of glycosylated residues serves to increase epitope recognition and antibody specificity.

A preferred embodiment of the fusion protein construct therefore is a unified molecule formed of two polypeptide fragments and having a length of 185 amino acid residues in sequence. The first residue is a Met—a start/allow expression in E. coli. The precise amino acid residue sequence formulation for this 185 residue length construct is given by Table 5; and the recombinant DNA sequence encoding this specific amino acid residue sequence is given by Table 6 below.

Note that within the amino acid sequence of Table 5, the two cysteines are changed to serine; and there is an extra isoleucine at position 47 in the HA2 residue sequence which is not present in the native HA2 fragment; and there is a short Leu-Asp-Gly sequence inserted between the HIV gp41 and HA2 fragments. This preferred formulation for the fusion protein construct shares significant primary, secondary, and tertiary structural similarities and parallels with the ectodomain of gp41; and is effective as both a systemic and mucosal antigen in-vivo. Moreover, an analysis of its crystalline structure (as described in the empirical results hereinafter) reveals the central portion or "core" for the first fragment to be alpha-helical in appearance and a rod-like oligomer.

TABLE 5

| Modified, gp41 HA fusion protein construct sequence |
|---|
| Met-Gln-Ala-Arg-Gln-Leu-Leu-Ser-Gly-Ile-Val-Gln- |
| Gln-Gln-Asn-Asn-Leu-Leu-Arg-Ala-Ile-Glu-Ala-Gln- |
| Gln-His-Leu-Leu-Gln-Leu-Thr-Val-Trp-Gly-Ile-Lys- |
| Gln-Leu-Gln-Ala-Arg-Ile-Leu-Ala-Val-Glu-Arg-Tyr- |
| Leu-Lys-Asp-Gln-Gln-Leu-Leu-Gly-Ile-Trp-Gly-Ser- |
| Ser-Gly-Lys-Leu-Ile-Ser-Thr-Thr-Ala-Val-Pro-Trp- |
| Asn-Ala-Ser-Trp-Ser-Asn-Lys-Ser-Leu-Glu-Glu-Ile- |
| Trp-Asn-His-Thr-Thr-Trp-Met-Glu-Trp-Asp-Arg-Glu- |
| Ile-Asn-Asn-Tyr-Thr-Ser-Leu-Ile-His-Ser-Leu-Ile- |
| Glu-Glu-Ser-Gln-Asn-Gln-Gln-Glu-Lys-Asn-Glu-Gln- |
| Glu-Leu-Leu-Glu-Leu-Asp-Lys-Trp-Ala-Ser-Leu-Trp- |
| Asn-Trp-Phe-Asn-Ile -Leu-Asp-Gly- Ala-Ile- |
| Asp-Gln-Ile-Asn-Gly-Lys-Leu-Asn-Arg-Val-Ile-Glu- |
| Lys-Thr-Asn-Glu-Lys-Phe-His-Gln-Ile-Glu-Lys-Glu- |
| Phe-Ser-Glu-Val-Glu-Gly-Arg-Ile-Gln-Asp-Leu-Glu- |
| Lys-Tyr-Val-Glu-Asp-Thr-Lys (SEQ ID NO: 3) |

TABLE 6

| Recombinant DNA Sequence | | | |
|---|---|---|---|
| ATGCAAGCAC | GCCAATTATT | GTCTGGTATA | GTGCAGCAGC |
| AGAACAATTT | GCTGAGGGCT | ATTGAGGCGC | AACAGCATCT |
| GTTGCAACTC | ACAGTCTGGG | GCATCAAGCA | GCTCCAGGCA |
| AGAATCCTGG | CTGTGGAAAG | ATACCTAAAG | GATCAACAGC |
| TCCTGGGGAT | TTGGGGTAGC | TCTGGTAAAC | TGATCAGCAC |
| CACTGCTGTG | CCTTGGAATG | CTAGTTGGAG | TAATAAATCT |
| CTGGAACAGA | TTTGGAATCA | CACGACCTGG | ATGGAGTGGG |
| ACAGAGAAAT | TAACAATTAC | ACAAGCTTAA | TACACTCCTT |

TABLE 6-continued

| Recombinant DNA Sequence | | | |
|---|---|---|---|
| AATTGAAGAA | TCGCAAAACC | AGCAAGAAAA | GAATGAACAA |
| GAATTATTGG | AATTAGATAA | ATGGGCAAGT | TTGTGGAATT |
| GGTTTAACAT | TCTAGATGGA | GCCATCGACC | AAATCATCAA |
| TGGGAAATTG | AACAGGGTAA | TCGAGAAGAC | GAACGAGAAA |
| TTCCATCAAA | TCGAAAAGGA | ATTCTCAGAA | GTAGAAGGGA |
| GAATTCAGGA | CCTCGAGAAA | TACGTTGAAG | ACACTAAA |
| (SEQ ID NO: 4). | | | |

Another major advantage evidenced by this preferred embodiment and shared by all embodiments of the fusion protein construct as a whole is the appreciable solubility in water and aqueous liquids generally in comparison to earlier used and conventionally known forms of the gp41 protein. The solubility of the present fusion protein constructs is unusually large, even in comparison to its immediate predecessors; and thereby renders this construct most suitable for use as an antigen in-vivo.

The appreciable solubility at physiological pH of the present fusion protein construct is demonstrated by the following evidence: (i) gp41 stays in solution after centrifugation; (ii) it forms soluble aggregates as judged by gel filtration chromatography and dynamic light scattering; (iii) gp41HA can be concentrated to at least 13 mg/ml or potentially higher; (iv) gp41 forms complexes with gp41 specific monoclonal antibodies, and specific binding to Fab fragments derived from monoclonal antibodies D31 and 2A2 can be observed (by gel filtration chromatography as well as by native gel electrophoresis) and gp41HA can be separated on native gel electrophoresis when complexed to Fabs derived from these gp41 specific monoclonal antibodies; (v) gp41HA is mostly alpha-helical in solution which is consistent with the structure of a core fragment of HIV-1 gp41. The replacement of the transmembrane region of gp41 by the influenza virus HA2 sequence induces a native-like structure of the amino acid sequence linking the outer core helix from residue 154 to residue 167. Together, these data indicate that gp41HA folds into a native-like structure which is therefore suitable for inducing conformation specific monoclonal antibodies, either IgG or IgA subtypes to neutralize HIV strains.

The major differences from other chimeric constructs previously reported in the scientific literature is therefore apparent. A prior art construct comprising extracellular residues of gp41 without the HA fusion part has been described; however this prior art construct is only soluble at low pH (<pH 4.0). Moreover, the earlier construct precipitates out of solution at physiological pH values and is thus not suitable or useful for immunization purposes [Caffrey et al., *EMBO J.* 17(16): 4572-84 (1998); Wingfield et al., *Protein Sci.* 6(8): 1653-60 (1997)].

Also, although a similar construct containing residues of gp41 and HA2 was published before [Weissenhorn et al., *PNAS* 94: 6065-6069 (1997)], the constructs described therein contained an additional sequence at the N-terminus (31 residues derived from an oligopeptide form of the GCN4 leucine zipper region) and proteolytic products thereof were then characterized. The basic construction of gp41HA as described herein and its biochemical and biophysical properties have therefore never existed before. Moreover, the construct used in the *PNAS* paper (named pIIgp41HA) was far less soluble than gp41HA and only produced soluble gp41 core fragments after proteolysis. These were also smaller fragments than gp41HA and contained less gp41 specific residues. In addition, the gp41 produced (as described in the PNAS paper) is monodispersed in solution and does not form soluble aggregates which are preferable to induce mucosal immunity.

Preferred Manner of Manufacture

A most desirable manner of making the preferred fusion protein construct of 185 amino acid residues in sequence is via recombinant DNA methods and systems. One preferred technique is summarized below.

A DNA fragment encoding an N-terminal methionine followed by residues 29 to 167 of HIV-1 gp41 (HXB2 strain) and residues 43 to 88 of influenza virus hemagglutinin subunit 2 was amplified by polymerase chain reaction using the plasmid pII41HA as a template. The nucleotide residues encoding cysteines at positions 88 and 94 of the gp41 protein had been previously mutated to encode serine residues to avoid intramolecular disulfide bond formation as described in Weissenhorn et al., *Proc. Natl. Acad. Sci. USA* 94: 6065-6069 (1997). The DNA fragment was cloned into expression vector pRset (Invitrogen) and introduced into *Escherichia coli* BL21/pUBS. The preferred fusion protein construct, referred to as gp41HA, was over-expressed in *E. coli* BL21/pUBS and purified from inclusion bodies with a final yield of 100 mg per liter of *E. coli* culture. GP41HA protein was solubilized in 8 M urea and frozen at −80° C. In vitro refolding was accomplished by dilution to a protein concentration of 50 M in 20 mM Hepes (N-[hydroxyethyl] piperazine-N'][2-ethanesulfonic acid]; Hepes; Sigma, Co.) [pH 8.0], which yielded soluble aggregates as judged by gel filtration chromatography. After refolding gp41HA could be concentrated to 13 mg/ml or higher and was stored at −80° C. Aliquots were thawed and diluted to 1 mg/ml in Hepes buffer (20 mM Hepes, pH 8.0) immediately prior to use.

The inclusion body preparation—using standard methods—yielded 99 percent purity as judged by SDS PAGE. Refolding can be accomplished at room temperature or at 4° C. resulting in approximately up to 80 percent yields. After refolding by dilution and concentration, gp41HA can be further purified by gel filtration chromatography; if necessary further purification on an ion exchange column can be achieved.

III. Immunogens And Vaccines

The essential component for the immunogens and vaccines of the present invention is the presence of at least one embodiment of the fusion protein construct as an active ingredient within the prepared fluid mixtures serving as immunogens and the adjuvant containing preparations serving as vaccines.

Immunogens

To be an immunogen, the formulation need only be a mixture of a fusion protein construct as described herein and a biocompatible carrier fluid suitable for carrying and delivering a predetermined aliquot of the fusion protein construct to a prechosen site in the body of a living subject.

Immunogens embodying the invention can be administered in any appropriate carrier for intradermal, subcutaneous, intramuscular, parenteral, intranasal, intravaginal, intrarectal, oral or intragastric administration. They can be introduced by any means that effect antigenicity in humans. The dosage administered will vary and be dependent upon the age, health, and weight of the recipient; the kind of concurrent treatment, if any; the frequency of treatment; and the nature of the humoral antibody response desired.

If the fusion protein construct is to be applied to a mucosal site (orally, intravaginally, intrarectally, intranasally or intragastrically), it can be admixed in a concentration from about 0.001 to 1,000.0 ug per gram of a pharmacologically inert carrier such as saline, and dextrose solutions. Other possible carriers are polyoxyethylene monolaurate 5% in water, sodium lauryl sulfate 5% in water, gastric acid inhibitors, protease inhibitors, pH neutralizers, and the like. Materials such as anti-oxidants, bumectants, viscosity stabilizers, and the like may be added, if necessary.

Similarly, if the immunogens are to be given intradermally, subcutaneously, intramuscularly, intravenously or parenterally, they will be prepared in sterile form; in multiple or single dose formats; and dispersed in a fluid carrier such as sterile physiological saline or 5% dextrose solutions commonly used with injectables. In addition, other methods of administration can be advantageously employed as well.

Vaccines

To be a prepared vaccine, the minimal formulation comprises a predetermined quantity of a fusion protein construct as described herein; a biocompatible carrier suitable for carrying and delivering a predetermined aliquot of a fusion protein construct to a prechosen site in the body of a living subject; and at least one adjuvant composition dispersed in the carrier fluid or coupled to the fusion protein construct. The vaccine, by definition, incorporates an immunogen and includes one or more adjuvants to facilitate or stimulate the immune response and to prolong the antigenic effect in-vivo over time.

Among the useful adjuvant substances conventionally known are those compositions approved by the FDA (currently or pending for systemic and/or mucosal immunizations). Some are preferred for mucosally-administered vaccines and others are preferred for intragastric administered vaccines.

In addition, for mucosal administration it is often desirable to also include one or more protease inhibitors in the overall formulation and recipe for a vaccine. Among the known protease inhibitor compounds deemed useful in a vaccine preparation are: aprotinin, leupeptin, AEBSF and bestatin. Any or all of these may be used at will with the present invention.

IV. Modes Of Administration

It is a particular goal of the present invention to induce mucosal IgA antibodies in-vivo which are specific against one or more epitopes of HIV-1. The objective of mucosal antibodies conforms to the mucosal vaccination strategies for women as recently published [Kozlowski et al., *J. Infect. Dis*. 179: S493-S498 (1999)], a strategic approach which serves men equally well with regard to potential HIV infections.

Multiple modes of inoculation, the manner of introducing an immunogen or vaccine, are conventionally known and used. The systemic or parenteral forms of administration (introduction by injection or perfusion) typically include intraperitoneal, intravenous, intramuscular, subcutaneous, and subdermal inoculations. In contrast, mucosal modes of administration may include not only the intranasal and intragastric forms of introduction, but also oral, intravaginal, and intrarectal introductions.

It has long been recognized that systemic administrations often produce different results from mucosal administrations of similar or identical substances. One major difference between the modes of administration is that in-vivo induction of IgA antibodies, especially secretory IgA antibodies, usually demands and requires using one or more forms of mucosal administration on at least one occasion; and typically requires multiple repeat inoculations over time using the same mucosal administration to be clinically effective. In comparison, if the same innoculum is systemically administered on one or multiple occasions, primarily serum IgG antibodies are produced in-vivo by the recipient of the immunogen or vaccine.

As evidenced by the experiments and empirical data described hereinafter, the present invention may be employed in the alternative to induce either serum IgG antibodies alone; or to induce both secretory IgA and serum IgG antibodies concurrently. The preferred mode of administration using the fusion protein construct as the immunogen or vaccine is to induce both anti-HIV IgA and IgG antibodies concurrently in the living host.

Method For Immunization

Although three different methods of immunization were tested in mice [as described in the experiments hereinafter], the focus of the mouse study was centered upon a method of immunization for the induction of both HIV-antigen specific IgA antibodies in mucosal secretions and IgG antibodies in serum in-vivo. This method comprises the steps of obtaining an immunogen (or vaccine) comprising a fusion protein construct and a biocompatible carrier fluid suitable for carrying and delivering a predetermined aliquot of the fusion protein construct to a prechosen anatomic site in the living subject; systemically administering an aliquot of the immunogen (or vaccine) on at least one occasion (and preferably on multiple occasions) to the body of the living subject as a primary immunization; and mucosally administering an aliquot of the immunogen (or vaccine) on at least one occasion (and preferably on multiple occasions) to a prechosen mucosal tissue site in the body of the living subject as a second immunization.

Illustrative Protocol

The following is presented as merely one example illustrative and representative of a clinical immunization protocol; and also serves as a basis for making the many different variants and procedural alternatives conventionally known and medically employed as immunization procedures to induce specific humoral antibodies in-vivo within the body of the recipient.

Preferences

It is most preferred that the immunogens and vaccines embodying the present invention be used as a systemic or mucosal boost by following a systemic prime/mucosal and/or boost regimen. The living recipient is first primed by a systemic injection since a systemic prime was shown previously to augment intestinal secretory IgA responses following subsequent mucosal boosts. A systemic prime followed by three intranasal (i.n.) or intragastric (i.g.) boosts will successfully induce serum IgG and fecal IgA antibodies that will recognize gp41 protein in both laboratory-adapted and primary isolates of HIV-1. In this manner, recombinant gp41 ectodomain is most useful as a mucosal antigen in prime-boost vaccine strategies to stimulate protective anti-HIV-1 S-IgA antibodies in humans. However, recombinant gp41HA may also be useful in protocols designed to induce systemic IgG antibodies primarily, as in systemic prime/systemic boost strategies.

Examplary Procedures for Administration by Parenteral and Mucosal Immunization Routes Immunization for Induction of Anti-gp41HA IgA Antibodies:

Although a combination of systemic and mucosal immunization routes were used in mice to test immunogenicity of gp41HA, immunization strategies utilizing mucosal administration routes alone (intranasal, peroral, intrarectal, and intravaginal) are more likely to generate greatest levels of anti-gp41 secretory IgA (S-IgA) antibodies in mucosal secretions of humans.

Based on results of previous human studies with other antigens, it is expected that intravaginal or intranasal immunization would produce greatest concentrations of anti-gp41 S-IgA (S-IgA) antibodies in genital tract secretions. Intranasal or intrarectal immunization, on the other hand, would likely prove most effective for generating anti-gp41 S-IgA antibodies in rectal secretions. Though peroral immunization has been found less effective for induction of specific IgA in the rectum and genital tract, peroral administration of gp41HA would be expected to induce greater levels of anti-gp41 IgA antibodies in small intestinal and salivary secretions, the latter of which could reduce or prevent oral transmission of HIV.

Studies in both mice and humans also suggest that intranasal immunization could be as effective as systemic immunization for induction of gp41-specific IgG antibody in the circulation. Hence, a combination of intranasal and rectal or vaginal immunization routes may be optimal for induction of anti-gp41 IgG in the bloodstream and anti-gp41 S-IgA in both genital tract and rectal secretions. Nevertheless, gp41HA IgA and IgG antibodies could be induced in humans using combinations of mucosal and systemic immunization routes.

Gp41HA Construct of Choice for Immunization:

If immunization is to be performed with a single gp41HA construct in the United States, it would be preferable to use gp41HA having a Clade B sequence (strains MN, HXB2, etc) since HIV-1 Clade B viruses predominate in North America. However, HIV-1 Clade A and E viruses are being detected more frequently in the U.S. population and, in the future, immunization with a combination of Clade A, B, and E sequence gp41HAs may be ideal.

Gp41HA Immunization Doses:

Based on the dosages of other recombinant HIV proteins administered in humans, it is likely that intramuscular, intradermal, and intranasal immunization with gp41HA would require a dose ranging from 50-500 μg. Oral, rectal, and vaginal immunizations would likely require greater gp41HA doses ranging from 250-1000 μg.

Number of Doses:

To obtain optimal immune responses, it is likely that gp41HA should be administered a minimum of 3 times within the first year. One annual booster immunization may be required for several years to maintain levels of circulating and secretory anti-gp41 antibodies.

Administration Schedule:

Further testing will be required to establish optimal immunization schedules. However, based on results of previous human mucosal immunization studies, it is anticipated that best results may be achieved if intranasal, intrarectal, peroral, or intravaginal immunization is performed a total of 3 times at biweekly or monthly intervals.

Detection of Antibody Responses:

Subjects are expected to demonstrate peak levels of circulating IgG and secretory IgA two weeks after the 3rd immunization. However, detectable antibodies should be present in sera and secretions two weeks after the 2nd immunization.

Procedures for Systemic or Mucosal Immunizations:

Form:

The following procedures are based on the assumption that gp41HA will be manufactured as a lyophilized powder in vials that must be reconstituted with 0.5 ml-1 ml water or sodium chloride diluent.

For Intramuscular Immunization:

1) The reconstituted contents of a vial will be drawn into a 1 cc syringe using a 1½ inch or 1 inch (for thin subjects) 22 gauge needle.

2) The solution will be injected into either the deltoid, quadriceps, or gluteal muscle.

For Intradermal Immunization:

1) The reconstituted contents of a vial will be drawn into a 1 cc syringe using a ½ inch 26-gauge needle.

2) The contents will then be injected into the arm above the deltoid or into the thigh above the quadriceps.

For Intranasal Immunization:

1) The reconstituted contents of a vial will be transferred into a sterile 1.5 ml vial using a 1 cc syringe equipped with a 1½ inch 22 gauge needle.

2) The syringe and needle will be discarded.

3) The solution of gp41HA will be drawn from the 1.5 ml tube into a sterile eye dropper.

4) The vaccine recipient will be asked to sit upright in a chair with head tilted back at an approximate 45 degree angle.

5) One drop of the gp41HA solution will be dispensed inside the left nostril near the opening of the passageway. A second drop will be similarly be added inside the right nostril. Immediately, the nostrils will gently be pinched shut to ensure coating of the entire nasal passage with solution.

6) Step 5 will be repeated until the entire contents of the gp41HA solution have been administered to the vaccine recipient.

For Peroral Immunization:

1) The reconstituted contents of a vial will be withdrawn using a syringe and 1½ inch 22 gauge needle.

2) The syringe contents will be ejected into a paper cup containing 150 mls of a stomach acid neutralizing sodium bicarbonate/water solution (e.g. alka seltzer).

3) The contents of the cup will be mixed using a sterile tongue depressor.

4) The subject will then ingest the contents of the paper cup.

5) The subject will refrain from eating or drinking (with the exception of water) for 2 hours.

For Intrarectal Immunization:

1) The reconstituted contents of a vial will be drawn through a 1½ inch 22 gauge needle into a 1 cc tuberculin syringe.

2) The needle will be discarded.

3) The subject will be placed on the exam table such that they are laying flat on their stomach or on their side.

4) The anus of the subject will be lubricated slightly with KY jelly.

5) The syringe will be inserted through the anus 6 cm into the rectum.

6) The subject will remain prone for 10 minutes.

For Intravaginal Immunization:

1) The contents of a vial will be reconstituted with 3 ml of diluent, then drawn slowly through a 1½ inch 22 gauge needle into the barrel of a 5 cc syringe previously loaded with 0.5 g of the inert powder Eldexomer (Perstorp, Sweden).

2) The needle will be discarded.

3) The subject will be placed on the exam table in supine position with feet in stirrups.

4) A vaginal speculum will be inserted.

5) The contents of the syringe will be deposited in the posterior fornix of the vagina.

6) The speculum will then be removed.

7) The subject will then remain prone for 10 minutes.

V. Experiments and Empirical Data

To demonstrate the merits and value of the present invention, a series of planned experiments and empirical data are presented below. It will be expressly understood, however, that the experiments described and the results provided are merely the best evidence of the subject matter as a whole which is the invention; and that the empirical data, while limited in content, is only illustrative of the scope of the invention envisioned and claimed.

Materials and Methods:

Preparation of Recombinant gp41.

A DNA fragment encoding an N-terminal methionine followed by residues 29 to 167 of HIV-1 gp41 (HXB2 strain) and residues 43 to 88 of influenza virus hemagglutinin subunit 2 was amplified by polymerase chain reaction using the plasmid pII41HA as a template. The nucleotide residues encoding cysteines at positions 88 and 94 of the gp41 protein had been previously mutated to encode serine residues to avoid intramolecular disulfide bond formation.

The DNA fragment was cloned into expression vector pRset (Invitrogen) and introduced into *Escherichia coli* BL21/pUBS. The gp41 fusion protein, referred to as gp41HA, was over-expressed in *E. coli* BL21/pUBS and purified from inclusion bodies with a final yield of 100 mg per liter of *E. coli* culture. GP41HA protein was solubilized in 8 M urea and frozen at −80° C. In vitro refolding was accomplished by dilution to a protein concentration of 50 M in 20 mM Hepes (N-[hydroxyethyl] piperazine-N'-[2-ethanesulfonic acid]; Hepes, Sigma Co.) [pH 8.0], which yielded soluble aggregates as judged by gel filtration chromatography. After refolding gp41HA could be concentrated to 13 mg/ml or higher and was stored at −8° C. Aliquots were thawed and diluted to 1 mg/ml in Hepes buffer (20 mM Hepes, pH 8.0) immediately prior to use.

Animals and Immunization Protocols.

Female BALB/c (H-$2^d$) mice 6-8 weeks of age were purchased from Charles River Laboratories (Wilmington, Mass.). They were housed in the Children's Hospital animal facility on standard rodent diet and allowed to acclimate for at least one week prior to this study. All experiments involving mice were done under strict compliance with the guidelines established by the NIH, Children's Hospital and Harvard Medical School.

There were three experimental groups and one control group of mice in this study. The three experimental groups were immunized ("primed") by a single intraperitoneal (i.p.) injection on day zero of 0.5 ml PBS (pH 7.4) containing gp41HA (50 g) and the systemic adjuvant N-acetylmuramyl-L-alanyl-D-isoglutamine (MDP; Calbiochem, La Jolla, Calif.) (50 g). Group one (n=4) was boosted systemically with the same dose given i.p. on days 7, 21 and 35. Mice in group two (n=6) were boosted intranasally (i.n.) on days 7, 21 and 35 with 40 l of PBS (pH 7.4) containing gp41HP (50 g), the mucosal adjuvant cholera toxin (1 g) (List Biological Laboratories, Campbell, Calif.), and protease inhibitors. The final concentrations of the protease inhibitors (Calbiochem, La Jolla, Calif.) were: aprotinin (50 U/ml), leupeptin (5 g/ml), AEBSF (48 g/ml), and bestatin (1 g/ml). Intranasal immunization was performed by lightly anesthetizing the mice with methoxyflurane (Pitmann-Moore, Mundelein, Ill.), then spotting 10 l of the gp41HA solution into each nare. The mice were allowed to recover and this procedure was repeated 2 hr later. Mice in group three (n-6) were boosted intragastrically (i.g.) on days 7, 21, and 35 with a sodium biocarbonate (0.1 M) solution (0.4 ml) containing gp41HA (250 g), cholera toxin (5 g) and protease inhibitors. Mice were deprived of food for 2 hrs before and 1 hr after i.g. immunization. I.g. immunization was performed on mice under light methoxyflurane anesthesia using a 1 cc syringe and a disposable 20G×1.5 inch blunt-ended feeding needle (Popper and Sons, New Hyde Park, N.Y.). Group four (n=4) was not immunized.

Serum and Feces Collection

Blood samples (0.2-0.4 ml) were collected via retro-orbital bleed from mice under avertin anesthesia seven days before the first immunization and 10 days after the final immunization. Avertin was prepared by dissolving 5.0 g tribromoethanol (Sigma Co.) into 10 ml of tertamyl alcohol (Fisher Co.), then diluting this solution 1:80 into pre-warmed (37° C.) PBS just prior to use. Aliquots of serum samples were stored at −80° C. Feces were collected six days before the first immunization and 7 and 14 days after the final immunization. Five or six freshly voided fecal pellets were collected from each mouse and placed into a pre-weighed Eppendorf tube containing 0.5 ml of PBS, 1% goat serum as blocking agent, and protease inhibitors. The tubes were then re-weighed and the weight of the feces in grams (average 0.1 g per mouse) was determined. The fecal suspensions were vortexed for 30 s, incubated on ice for 20 min, and the insoluble material was removed by centrifugation for 10 min at 12,000×g. The resulting fecal extract was passed through a 0.45 m filter (Millipore Co), collected into a 1.5 ml microfuge tube, and aliquots (0.1 ml) were stored at −80° C.

Enzyme-Linked Immunosorbent Assays (ELISA)

For anti-gp41HA ELISAs, 0.1 ml of gp41HA (1 g/ml) in 20 mM HEPES buffer (pH 8.2) was applied to each well of a 96 well of Nunc-Immuno plate (Maxisorp F96; A/S Nunc, Roskilde, Denmark). Plates were incubated overnight at 4° C. in a humidified chamber, washed with PBS containing Tween-20 (0.05% v/v), then blocked with PBS containing Tween-20 (0.05%) and goat serum (1% v/v) for 1 hr at 37° C. Serum or fecal samples were serially diluted into blocking buffer then applied to each well (100 l/well) and incubated for 2 hr at room temperature (23° C.) in a humidified chamber. The plates were washed, overlaid with affinity-purified, peroxidase-conjugated, goat polyclonal antibodies (Southern Biotechnology Associates, Inc. (SBA), Birmingham, Ala.) specific for either the alpha chain of mouse IgA (1 g/ml) or the gamma chain of mouse IgG (0.5 g/ml). Plates were developed using the one-component TMB substrate as suggested by the manufacturer (Kirkegaard & Perry Laboratories, Gaithersburg, Md.). For all assays an anti-gg41 mouse monoclonal IgG antibody which recognizes an epitope located between amino acids 730 and 750 (ImmunoDiagnostics, Inc., Bedford Mass.) was used as a positive control.

HIV-specific and total IgA and IgG in feces and serum was determined by ELISA essentially as previously described [Kozlowski et al., AIDS Res. Hum. Retroviruses 10: 813-822 (1994)]. Nunc MaxiStop microtiter plates were coated with 3.3 g/ml HIV-1$_{IIIB}$ viral lysate (Cambridge Scientific, Rockville, Md.), 3.3 g/ml HIV-1$_{MN}$ viral lysate (Advanced Biotechnologies Inc., Columbia, Md.), or 1 g/ml affinity-purified goat anti-mouse IgA antibodies (ICN, Aurora, Ohio). Purified mouse myeloma IgA (SBA) was used as a standard in total IgA assays, and the anti-gp41 monoclonal IgG antibody (described above) was used as the standard for all HIV-1$_{MN}$ and HIV-1$_{IIIB}$ assays.

Western Blot Analysis

HIV-1 lysate Western blot strips were from Calyptebiomedical (Alameda, Calif.). Nitrocellulose strips were incubated for 2 h in blocking buffer (PBS containing goat serum (2% v/v) and Tween-20 (0.1% v/v) at room temperature, then overnight in serum samples (diluted 1:250 into blocking buffer) or fecal samples (diluted 1:50 in blocking buffer). The strips were then washed and incubated with biotin-conjugated, goat-polyclonal antibodies specific for the gamma chain of mouse IgG (0.5 g/ml; SBA) or the alpha chain of mouse IgA (0.5 g/ml; SBA), followed by peroxidase-conjugated avidin (2 g/ml). The strips were developed using the ECL chemiluminescent detection system (Amersham-Pharmacia Biotech, Piscataway, N.J.) and Kodak X-OMAT film.

Infection of Cells with HIV-1

H9 T cells (American Type Culture Collection, Rockville, Md.) chronically-infected with the HIV-1$_{IIIB}$ clone, HIV-1$_{HXB2}$ (provided by Dr. Anna Aldovini, Children's Hospital, Boston, Mass.), were established after inoculating 1×10$^6$ cells with 2.5×10$^4$ TCID$_{50}$ viral stock. Cells surviving acute infection were maintained at >90% viability by splitting cultures 1/10 every 3 d in RPMI 1640 containing 25 mM HEPES, 600 g/ml L-glutamine, 100 units/ml penicillin, 100 g/ml streptomycin (Life Technologies, Grand Island, N.Y.) and 20% fetal bovine serum (FBS; BioWhittaker, Walkersville, Md.). The TCID50/ml of the HIV-1$_{HXB2}$ stock was determined by endpoint titration in H9 cells using methods described for peripheral blood mononuclear cells (PBMC) [40] except that 5×10$^4$H9 cells were placed in each 96 well on day 0 and cells were split 1/10 on day 4. For neutralization assays a fixed viral inoculum (75 TCID$_{50}$/well) was preincubated with mouse sera, fecal extracts, or monoclonal control antibodies prior to being mixed with H9 cells. HIV-1 treated cells were assayed for p24 production as described previously [Kozlowski et al., AIDS Res. Hum. Retroviruses 10: 813-822 (1999)].

To obtain cells infected with HIV-1 primary isolates, PBMC were isolated from normal blood by standard density gradient centrifugation on Ficoll-Paque (Amercham-Pharmacia) and 1×10$^7$ cells were cultured for 3 d with 2.5 g/ml phytohemagglutinin (Sigma Co.) in 10 ml of complete RPMI 25 cm² flask. The cells were then washed, adjusted to 1×10⁶/ml in 10 ml medium containing 5% IL-2 (Hemagen, Columbia, Md.), and returned to their original flask. The PBMC were then inoculated with 1 ml of culture supernatant containing an HIV primary isolate (all 1-5×10⁴ TCID50/ml). Cultures of uninfected control PBMC from the same donor were established in parallel and maintained in flasks for 2-3 wk with ½ splitting at 3-4 d intervals in IL-2 supplemented medium.

HIV primary isolates were the gift of Dr. Robert Husson (Department of Medicine, Children's Hospital, Boston, Mass.). These isolates were obtained from infected women by co-culture technique and were previously characterized as syncytium-inducing (SI) or non-SI (NSI) using the MT-2 T cell line [Husson et al., *J. Pediatr.* 126: 865-871 (1995)]. "Macrophage tropic" NSI isolates replicate in activated primary T cells but not T cell lines [Unutmaz et al., *Proc. Natl. Acad. Sci. USA* 94: 1615-1618 (1997)]. A highly cytopathic SI isolate that produced syncytia in PBMC cultures was selected for use in this study. An NSI isolate that consistently produced no syncytia when propagated in PBMCs was chosen. Infection of NSI-inoculated PBMC cultures was confirmed by screening culture fluid for HIV p24 antigen using a commercially available ELISA kit (NEN, Boston, Mass.).

Immunocytochemistry of HIV-1 Infected Cells

Slides of NSI- or SI-infected PBMC were prepared on post-infection days 10 to 14. Slides of control uninfected cultured PBMC from the same donor were prepared in parallel. Suspensions of PBMC were first subjected to density gradient centrifugation on Ficoll-Paque to remove dead cells, and then washed 3 times with Dulbecco's PBS (DPBS) containing 5% goat serum and adjusted to 2×10⁶ cells/ml. Aliquots of cells in suspension (150 l) were then centrifuged for 4 min at 750 rpm onto glass slides using a Cytospin 3 (Shandon-Lipshaw, Pittsburgh, Pa.). After centrifugation slides were transferred to staining jars containing 100% acetone, which were placed at −20° C. overnight. Slides were then rinsed 3 times with PBS and stored at 4° C. immersed in PBS with 0.1% azide. Cytocentrifuge slides of H9 cells or H9 cells infected with HIV-1$_{HXB2}$ were prepared as described above except that cells were suspended at 1×10⁶ cells/ml prior to centrifugation.

NSI and SI cytocentrifuge slides were screened by immunostaining using a rabbit anti-p24 polyclonal antibody (Advanced Biotechnology Incorporated, Columbia, Md.) to determine which preparations contained greatest numbers of infected cells. To evaluate mouse sera and fecal extracts for the presence of IgG and IgA antibodies that recognize native viral gp41 on the surfaces or within the cytoplasm of infected cells, cytospin slides were washed three times in PBS, blocked with PBS containing Tween-20 (0.05% v/v) and goat serum (1% v/v), then overlaid with serum samples (diluted 1:50 into blocking solution) or fecal extracts (diluted 1:10 into blocking solution) for 2 hr at room temperature. After washing, slides were treated with biotin-conjugated, goat polyclonal antibodies specific for either the alpha chain of mouse IgA (20 g/ml) or the gamma chain of IgG (20 g/ml) for 1 hr, washed, and then stained with fluorescein-conjugated streptavidin (SA-FITC; 2 g/ml, Pierce Chemical Co., Rockford, Ill.). Slides were post-fixed for 5 min in 2% paraformaldehyde (v/v) in PBS, then mounted with Moviol [0.5 g/ml glycerol, 0.1 g/ml Mowiol 4-88 (Calbiochem, San Diego, Calif.), 10 mg/ml diazbicylo[2.2.2]octane (Sigma Co.) in 0.1M Tris-HCl (pH 8.5)]. Slides were viewed using a BioRad MRC 1024 confocal laser-scanning microscope at the Harvard Digestive Disease Center Core Facility. Images were collected using the BioRad imaging software and edited using Abode Photoshop 5.0.

Experimental Series I

Experiment 1

Systemic and Mucosal Immunogenicity of gp41HA

To test whether the recombinant gp41 protein gp41HA is immunogenic in mice when used in a systemic prime/mucosal boost regimen, groups of mice were primed intraperitoneally (i.p.), then boosted either i.p., intranasally (i.n.) or intragastrically (i.g.) three times at two-week intervals, as described in the Materials and Methods. Serum and fecal extracts were collected 7 and 10 days after the last immunization and screened by ELISA for reactivity to gp41HA antigen.

Antibody levels in fecal extract can serve as an indicator of secretory antibodies in the gastrointestinal tract of mice. The average reciprocal endpoint titer of gp41HA-specific IgG in sera of mice in all immunized groups exceeded 600,000 on day 7, whereas reciprocal endpoint titers in pre-immune sera or unimmunized controls were less than 100 (data not shown). High levels of anti-gp41HA IgA antibodies were detected in fecal extracts collected on day 10 from i.n. and i.g. immunized mice (mean reciprocal endpoint titer >10,000)—but not in extracts from i.p. immunized mice (<160) or non-immunized controls (<80). These data demonstrate that the gp41HA fusion protein was immunogenic in mice; and that mucosal boosts were necessary to evoke secretory IgA antibodies.

Experiment 2

HIV-1 Specific IgG in Serum of Systemically and Mucosally Immunized Mice

Because gp41HA is a recombinant fusion protein containing portions of both HIV-1 gp41 and influenza HA, the gp41HA ELISA data of Experiment 1 did not indicate whether gp41-specific antibodies were induced in these animals. Therefore, in this experiment, the serum samples were analyzed by ELISA for reactivity to gp41 in HIV-1$_{IIIB}$ viral lysate. The empirical results are shown graphically by FIGS. 2A and 2B respectively.

Figure 2A:
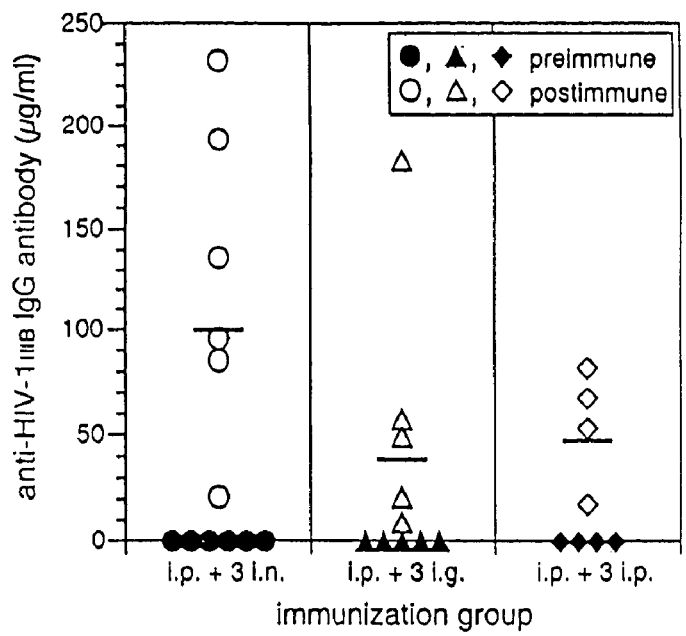
FIGS. 2A and 2B are graphs empirically demonstrating the presence of HIV-1 specific IgG antibodies in the serum of systemically and mucosally immunized mice.
Figure 2B:
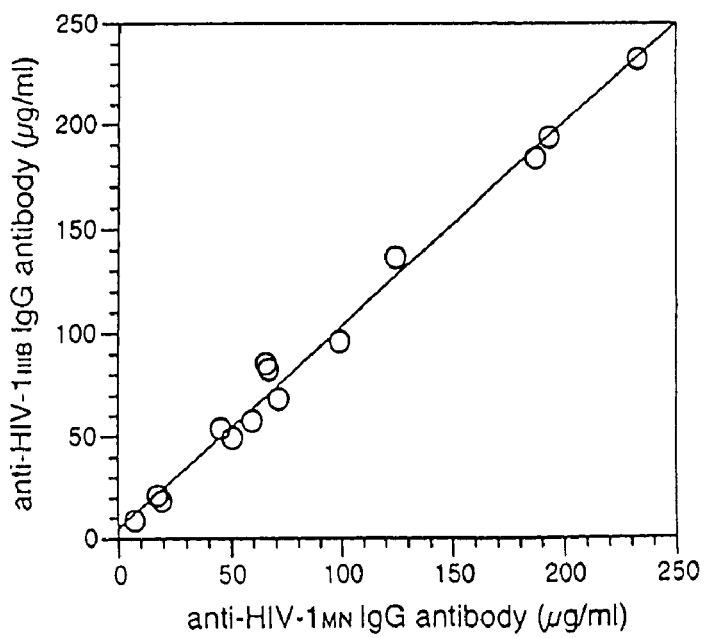

FIG. 2 as a whole demonstrates that HIV-specific IgG antibodies are induced in serum. FIG. 2A shows geometric mean (bars) and individual concentrations of anti-HIV-1$_{IIIB}$ IgG antibody quantitated by ELISA in serum of mice before immunization and 10 days after the last immunization with gp41HA. FIG. 2B shows the concentrations of anti-HIV-1IIIB and anti-HIV-1$_{MN}$ IgG antibodies measured in day 10 serum of all immunized mice. Geometric mean concentrations of anti-HIV-1$_{IIIB}$ IgG in preimmune serum of mice in the i.n., i.g., and i.p. immunization groups were 0.064, 0.066, and 0.068 g/ml, respectively. For each group, post-immune antibody concentrations were determined to be significantly greater than those in corresponding preimmune serum using the two-tailed paired t-test.

As shown in FIG. 2A, an i.p. prime followed by three i.n., i.g., or i.p. boosts with gp41HA induced significant concentrations of serum anti-HIV-1$_{IIIB}$ IgG antibodies. The geometric mean reciprocal endpoint titers measured in these sera were 86,000 (i.p./i.n.), 24,000 (i.p./i.g.), 31,000 (i.p./i.p.), as compared to less than 50 for all pre-immune samples. Although the i.p./i.n. immunized mice tended to have the highest levels of HIV-1$_{IIIB}$-specific serum IgG antibodies, there were no statistical differences between the three groups of immunized mice. Thus, each prime/boost regimen was equally effective at inducing anti-gp41 specific systemic IgG antibodies.

Serum samples were also tested by ELISA for reactivity to gp41 in viral lysate of HIV-1$_{MN}$, another laboratory-adapted T cell tropic HIV isolate. Regardless of immunization route, post-immune serum from all mice contained significant concentrations of anti-HIV-1$_{MN}$ IgG antibodies as revealed by FIG. 2B. Analysis of individual samples showed a strong correlation (p<0.0001) between the concentration of anti-HIV-1$_{MN}$ IgG antibodies and anti-1$_{IIIB}$ IgG antibodies. The extent of cross-reactivity to HIV-1$_{MN}$, estimated by dividing concentrations of anti-HIV-1$_{MN}$ IgG by anti-HIV-1$_{IIIB}$ IgG antibody, was determined to average 94%.

Experiment 3

Levels of Anti-HIV-1 Specific IgA Antibodies in Fecal Extracts

To determine whether systemic prime followed by mucosal boosts with gp41HA induced mucosal IgA antibodies to gp41, fecal; extracts from immunized mice were examined by ELISA for IgA antibodies to HIV-1$_{IIIB}$ viral lysate. Because an anti-gp41 monoclonal IgA standard was not available, the concentrations of anti-HIV-1$_{IIIB}$ IgA antibodies were estimated using as a standard the anti-gp41 IgG monoclonal antibody described above. In interpreting these results, one is aware of the fact that intestinal IgA antibodies are generally in dimeric (or oligomeric) form; and consequently, it is likely that concentrations of specific IgA were underestimated by a factor of 2.5 when using an IgG standard.

Postimmune fecal extracts from mice in the i.p./i.n. and i.p./i.g. immunization groups both demonstrated mean reciprocal endpoint titers of 220 and mean concentrations of 6 g/ml anti-HIV-1$_{IIIB}$ IgA antibody. It is known that total IgA immunoglobulin concentrations can vary widely in fecal samples [Haneberg et al., *Infect. Immun.* 62: 15-23 (1999)]. Therefore, to more accurately compare the levels of specific intestinal IgA in fecal extracts, the HIV specific activity in each extract was calculated and is presented in FIG. 2.

Figure 3:
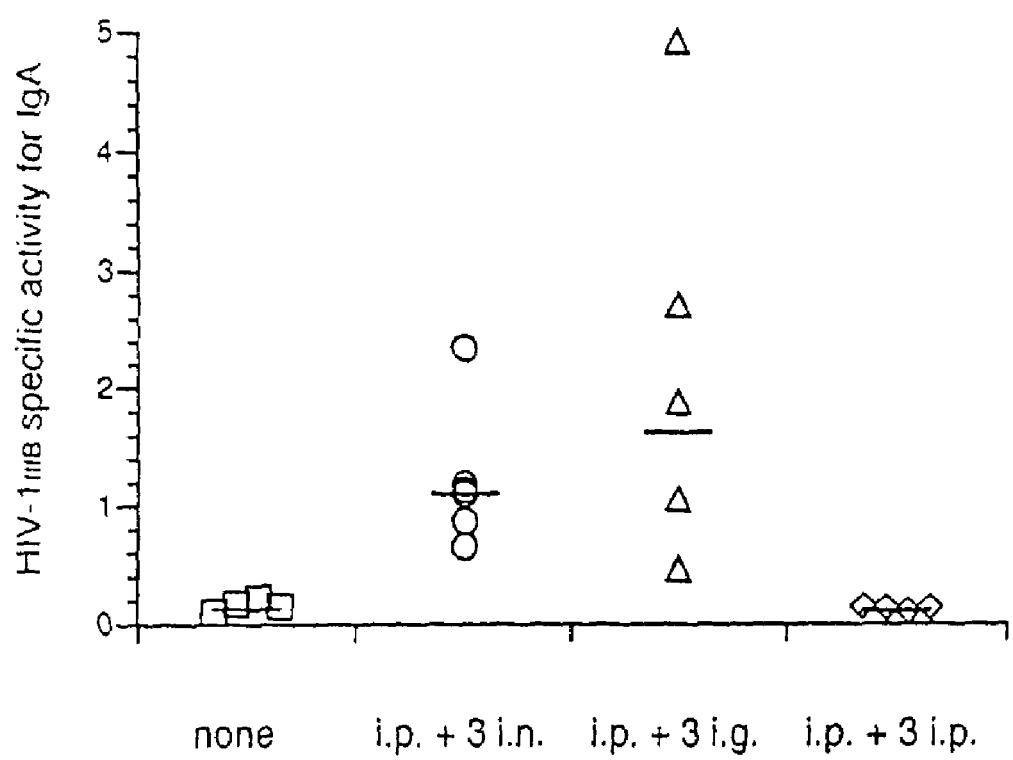
FIG. 3 is a graph presenting the levels of anti-HIV specific IgA antibodies in fecal extracts.

FIG. 3 is a graph demonstrating the presence of HIV-specific IgA antibody in fecal extracts from gp41HA immunized mice. As seen therein, the concentrations (g/ml) of anti-HIV-1$_{IIIB}$ IgA antibody were divided by total IgA concentration (g/ml) in fecal extracts to obtain HIV-specific activity for IgA. The specific activity×100 measured in extracts prepared from feces of non-immunized mice and those collected from gp41HA immunized mice is shown 7 days after the last immunization. The bars represent geometric means. The fecal extracts from mice in the i.n. and i.g. groups were determined by ANOVA to contain significantly greater HIV-specific IgA activity than those from non-immunized and i.p. immunized mice.

The empirical data reveals that fecal extracts from mice boosted by either i.g. or i.n. routes demonstrated significantly greater HIV specific activity than those from mice in the i.p. or non-immunized control groups (p<0.0001 by ANOVA). There was no statistical difference between the average specific activity of IgA in feces from i.g. boosted mice (mean 1.6) and from i.n. mice (mean 1.1); and both of these values were greater than the respective mean specific activities (i.g. 0.3; i.n. 0.8) determined for IgG in serum of these animals (data not shown). Like anti-HIV-1$_{IIIB}$ IgG serum antibodies, anti-HIV-1$_{IIIB}$ IgA in i.n. and i.g. fecal extracts cross-reacted with HIV-1$_{MN}$ viral lysate (not shown), and concentrations of specific IgA measured in these two ELISAs were highly correlated (p<0.0001). Thus, these results show that systemic prime followed by mucosal boosting with gp41HA can induce anti-gp41 specific IgA antibodies in mucosal secretions and anti-gp41 specific IgG antibodies in serum.

Experiment 4

Western Blot Analysis of Serum IgG and Fecal IgA Antibodies

To confirm the gp41 specificity of serum IgG and fecal IgA antibodies, we examined the reaction patterns of sera and fecal extracts on HIV-1$_{IIIB}$ Western blot strips. The results of these analyses are presented by FIG. 4.

Figure 4:
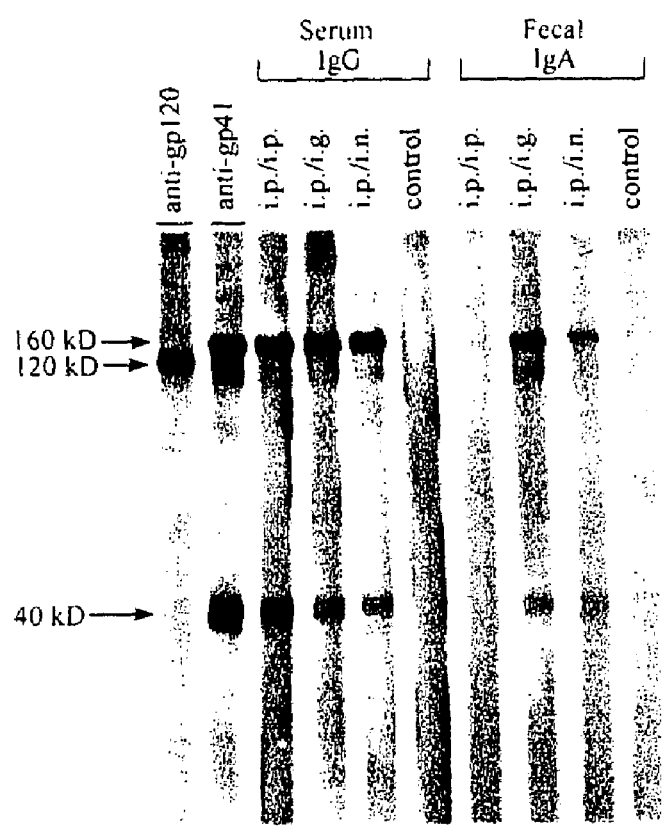
FIG. 4 is a photograph showing the Western blot analysis of serum IgG and fecal IgA antibodies.

FIG. 4 shows that anti-gp41HA serum IgG and fecal IgA antibodies react with monomeric and oligomeric gp41. HIV-1$_{IIIB}$ lysate Western blot strips (Calypte Biomedical, Alameda, Calif.) were probed with monoclonal anti-HIV envelope antibodies, anti-p41HA antisera, or fecal extracts from gp41HA immunized mice. As described in the Materials and Methods, anti-sera or fecal extracts from groups of mice were pooled and diluted 1:250 or 1:50, respectively, before being used for Western blot analysis. Monoclonal IgG antibodies and serum IgG antibodies were detected using affinity purified goat IgG antibodies for the Fc fragment of mouse IgG. Fecal IgA antibodies were detected using affinity purified goat antibodies specific for the alpha chain of mouse IgA. A single protein band of approximately 120 kD corresponding to gp120 was present on strips probed with a mouse monoclonal anti-gp120 IgG (ImmunoDiagnostics) antibody. The mouse monoclonal anti-gp41 antibody 2A2 revealed three bands at apparent molecular weights of 40 kD, 120 kD and 160 kD, corresponding to monomeric and oligomeric forms of gp41.

In particular, FIG. 4, lane a shows an anti-HIV-1$_{IIIB}$ V3 loop monoclonal antibody (ImmunoDiagnostics) that recognizes both gp120 and gp160 labeled a single band of approximately 120 kD on these strips. An anti-gp41 monoclonal IgG antibody (ImmunoDiagnostics) which reacted strongly with proteins of approximately 40 kD and 160 kD is shown by FIG. 4, lane b, and appears weakly with a protein of approximately 120 kD.

The diffuse band at 40 kD presumably corresponds to monomeric glycosylated gp41. The band of approximately 160 kD was not gp160 since it was not labeled with anti-gp120 monoclonal antibodies (FIG. 4, lane a). Rather, this 160 kD band and the faint band of 120 kD in lane b is believed to reflect the presence of disulfide-linked gp41 oligomers present in certain commercial Western blot strip preparations [Zolla-Pazner et al., *New Eng. J. Med.* 320: 1280-1281 (1989)].

By Western blot analysis serum, IgG antibodies from i.p., i.p./i.n. and i.p./i.g. gp41HA immunized mice reacted with proteins of 40 kD and 160 kD (FIG. 4, lanes c-e) with a pattern identical to that which was obtained with the commercial monoclonal anti-gp41 antibody. Pre-immune mouse serum did not react with any proteins present in HIV-1 lysate (FIG. 4, lane f), in agreement with data obtained previously by ELISA.

To determine whether the fecal IgA antibodies were specific for gp41, Western blot strips were incubated in fecal extracts, then developed using goat anti-mouse IgA antibodies. IgA antibodies in fecal extracts from i.p./i.g. and i.p./i.n.

immunized mice reacted with proteins at 160 and 40 kD, corresponding to monomeric and oligomeric gp41 (FIG. 4, lanes h-i). There were no detectable anti-gp41 IgA antibodies present in fecal extracts from i.p. immunized mice (FIG. 4, lane g) or unimmunized controls (FIG. 4, lane j).

Experiment 5

Neutralization of HIV-1 Infection In-Vitro

Serum and fecal extracts from gp41HA immunized mice which contained the highest concentrations of anti-HIV-1$_{IIIB}$ antibody by ELISA were then tested in vitro for their ability to neutralize HIV-1$_{IIIB}$ infections of H9 T cells. Preincubation of virus with 10 g/ml of neutralizing anti-gp120 IgG monoclonal antibody used as a positive control reduced viral infection of these cells by 99% whereas an identical concentration of isotype-matched anti-Epstein Barr virus monoclonal antibody had no effect (data not shown). Similarly, pooled human HIV-positive sera (diluted 1/40) was found to reduce infection by 63% compared to the same dilution of pooled HIV-negative sera. However, viral levels in cell cultures containing post-immune mouse serum diluted 1/20-1/80 did not differ significantly from those in cultures with corresponding preimmune serum dilutions. Potential neutralization by IgA in fecal extracts could not be assessed because both preimmune and postimmune fecal extracts caused cell death after 3 days of culture, even at dilutions >1/100.

Experiment 6

Serum IgG and Fecal IgA Antibodies Recognize Peripheral Blood Mononuclear Cells Infected with HIV-1 Primary Isolates Although mouse anti-gp41HA serum antibodies were unable to protect a T cell line from infection by cell-free HIV-1$_{IIIB}$ in vitro, this tissue culture assay does not reflect the mechanism of protection that is most important on mucosal surfaces in vivo. Attachment of SIgA antibodies to viral surface proteins could induce viral aggregation and entrapment in mucus layers on vaginal and rectal surfaces in an environment devoid of target cells such as T cells [Lamm, M. E., Ann. Rev. Microbiol. 51: 311-340 (1997)]. IgA in mucosal secretions that can bind virus or virus-infected cells may be sufficient to reduce HIV infection of mucosal tissues in vivo. Thus this experiment sought to determine whether the anti-gp41HA IgA antibodies in mouse fecal samples recognized gp41 from a primary, clinically relevant "T cell-tropic" SI isolate and a "macrophage-tropic" NSI isolate.

Peripheral blood mononuclear cells (PBMC) were infected with primary SI or NSI HIV-1 isolates and probed by indirect immunofluorescence with serum and fecal extracts from preimmune or gp41HA immunized mice that showed the highest anti-gp41 titers by ELISA. The results are shown by FIGS. 5A-5F respectively; and should be compared to FIGS. 6A-6D as well.

FIG. 5 as a whole demonstrates that serum IgG and fecal IgA from gp41HA immunized mice react with PBMCs infected with NSI isolate. FIG. 5A shows mouse monoclonal IgG and anti-gp41 antibody 2A2. FIG. 5B shows unimmunized mouse serum IgG. FIG. 5C shows i.p./i.n. serum IgG. FIG. 5D shows i.p./i.g. serum IgG. FIG. 5E shows i.p./i.n. fecal extracts. FIG. 5F shows unimmunized mouse fecal extracts.

In particular, FIG. 5A reveals cytospin preparations of PBMCs infected with a primary NSI isolate which were probed with monoclonal anti-HIV envelope antibodies; while FIGS. 5B-5D show anti-gp41HA antisera and FIGS. 5E-5F show fecal extracts from gp41HA immunized mice. Monoclonal IgG antibodies and serum IgG antibodies were detected using biotinylated goat IgG antibodies specific for the Fc fragment of mouse IgG and SA-FITC. Fecal IgA antibodies were detected using affinity purified goat antibodies specific for the alpha chain of mouse IgA and SA-FITC.

In contrast, FIG. 6 as a whole demonstrates that fecal IgA antibodies from gp41HA immunized mice react with PBMCs infected with an HIV-1 SI primary isolate. FIG. 6A shows anti-gp41 monoclonal antibody 2A2; FIG. 6B shows unimmunized mouse fecal extract; FIG. 6C shows i.p./i.g. fecal extract; and FIG. 6D shows i.p./i.g. fecal extract.

In particular, cytospin preparations of PBMCs infected with a primary SI isolate were probed with a monoclonal anti-HIV gp41 antibody (FIG. 6A) or fecal extracts from gp41HA immunized mice (FIGS. 6C-6D). Immunocytochemistry was performed as described in the legend to FIG. 5.

These empirical results reveal and demonstrate that infection of PBMC with primary HIV-1 isolates gives rise to an asynchronous, heterogeneous population of cells, some which are heavily infected with virus and some which remain uninfected. The monoclonal anti-gp41 antibody 2A2 strongly labeled a sub-population of cells in both NSI- (FIG. 5A) and SI-infected (FIG. 6A) PBMC acetone-fixed cytospin preparations, but did not label uninfected PBMC controls. Because acetone fixation permeabilizes cells, we were unable to determine whether the monoclonal antibody was staining cell surface-associated gp41, intracellular gp41/gp160, or both. Serum IgG from mice boosted with gp41HA i.p. (data not shown), i.n. (FIG. 5C) and i.g. (FIG. 5D) labeled a sub-population of cells in the NSI-infected (FIG. 5) and SI-infected (data not shown) PBMC cultures with a frequency similar to that observed with the gp41 monoclonal antibody control. Serum IgG from unimmunized control mice did not stain NSI- or SI-infected PBMCs (FIG. 5B).

To determine whether anti-gp41HA IgA antibodies in feces reacted with NSI- or SI-infected PBMCs, cytospin preparations were overlaid with fecal extracts (diluted 1:10), then developed using biotinylated goat anti-mouse IgA antiserum and streptavidin fluorescein. Fecal IgA from mice mucosally boosted with gp41HA labeled a sub-population of cells within the NSI-infected (FIG. 5) and SI-infected (FIG. 6) PBMCs cytospin preparations with a pattern and frequency similar to that obtained with the gp41 control IgG antibody. Fecal extracts from i.p. boosted mice (data not shown) or unimmunized control mice (FIGS. 5 and 6) did not react with infected cells. These data indicate that anti-gp41HA serum IgG and fecal IgA antibodies recognize gp41 from clinically relevant HIV-1 isolates.

Conclusions Supported by the Data of Experimental Series I

1. The immunogenicity of the preferred construct, gp41HA, a recombinant protein containing the ectodomain of gp41 from HIV-1$_{IIIB}$ is empirically demonstrated in-vivo. The systemic prime-mucosal boost regimens with gp41HA induced anti-gp41 IgG antibodies in serum and IgA antibodies in secretions that recognized laboratory adapted and primary isolates of HIV-1. Although performed in mice, these data are significant because they demonstrate that a recombinant form of gp41 is immunogenic when given mucosally and is capable of stimulating S-IgA antibodies against clinically relevant HIV-1 isolates.

2. The fusion protein construct, gp41HA, shares significant primary, secondary, and tertiary structure with the ectodomain of gp41; and this accounts for its observed effectiveness as both a systemic and mucosal antigen. The gp41HA protein contains 138 amino acids—a sequence representing 90% of the native gp41 ectodomain. In contrast to gp120 (which contains multiple hypervariable domains), the primary amino acid sequence of the gp41 ectodomain is relatively conserved among HIV-1 isolates from different clades worldwide. Indeed, the amino acid sequence of the ectodomain of gp41 from HIV-1$_{IIIB}$ differs from HIV-1$_{MN}$ by only 5 amino acids.

3. Analysis of the crystal structure of the central portion or "core" of the gp41 ectodomain indicates that it forms a-helical, rod-like oligomers. The fusion protein construct gp41HA assumes a folded conformation and has an a-helical content similar to the core of gp41. Moreover, because native gp41 is believed to assemble in the viral membrane as a trimer, the gp41HA protein is believed also to assume a similar tertiary structure—since two mouse monoclonal antibodies D31 and 2A2 (each of which recognizes conformational dependent epitopes on oligomeric gp160) bind gp41HA.

4. Two notable differences exist between the fusion protein construct gp41HA and native gp41. The first is: due to site-directed mutations in the highly conserved cysteine residues at positions 88 and 94, gp41HA cannot and does not make the intramolecular disulfide bond necessary for the formation of the immunodominant loop. The second is: gp41HA was produced in *E. coli* hosts and consequently lacks the four N-linked carbohydrate side chain modifications normally present on the gp41 ectodomain. This has substantial immunological consequences since immunization of macaques with nonglycosylated gp120, as compared to glycosylated gp120, resulted in a broadened humoral immune response and enhanced neutralizing antibody titers against wild-type, glycosylated virus.

5. The present invention (and the empirical data described hereinafter which factually evidence and support the invention) are a reaffirmation of the differences in the specific mode of administration: the induction of antigen specific S-IgA antibodies in mucosal secretions occurs after mucosal but not after systemic immunization. Whereas the three prime-boost immunization strategies empirically tested (i.e., i.p./i.p.; i.p./i.n.; i.p./i.g.) were each equally effective at inducing anti-HIV-1 serum IgG antibodies in mice, only the i.p./i.n. and i.p./i.g. modes of administration gave rise to anti-go41 IgA antibodies in feces. Thus, the present invention demonstrates that secretory antibodies are initiated only after antigens are delivered via transepithelial transport into organized lymphoid tissue located within the mucosa or in nearby lymph nodes, where antigen specific mucosal B cells are generated. The presence of anti-gp41HA antibodies following i.g. and i.n. immunization are ample evidence to indicate that gp41HA was sampled by the mucosa of both the gut-associated and nasal-associated lymphoid tissues.

6. The present invention also is supporting evidence that soluble non-adherent protein antigens are weak mucosal antigens because they are inefficiently sampled by the MALT and/or are rapidly degraded by proteases present in secretions. The efficacy of gp41HA as a mucosal antigen is believed to be primarily due to the fact that the recombinant protein aggregates in solution, as determined by gel filtration chromatography and native gel electrophoresis (Weissenhorn et al., unpublished results). Aggregated proteins are believed to be better mucosal antigens than soluble proteins because they are more resistant to mucosal proteases and are more effectively sampled by the follicle-associated epithelium.

7. Intranasal immunization is an especially appealing route for delivery of vaccines against sexually transmitted diseases like HIV-1 because of its ability to stimulate S-IgA antibodies in both local and distant mucosal secretions. The appearance of antigen specific IgA at distant mucosal sites following i.n. immunization is believed due to the emigration of antigen specific B cells from the nasal associated lymphoid tissue. In addition, intranasal immunization stimulates the cellular immune responses. For example, i.n. (but not i.p.) immunization of mice with recombinant proteins induced antigen specific cytotoxic T lymphocytes in the female genital tract, spleen and cervical lymph nodes.

8. It is essential to recognize and appreciate that systemic immunization alone with the fusion protein construct gp41HA failed to induce detectable neutralizing serum IgG antibodies, as determined by the T cell protection assay. This fact is not surprising since neutralizing epitopes on gp41 are rare and/or poorly presented to the immune system.

9. As empirically described hereinafter, the fact that secretory anti-gp41HA IgA antibodies recognized PBMCs infected with primary HIV-1 isolates shows that secretory antibodies evoked by gp41HA immunization in humans will likely have a protective capacity in vivo. Whereas serum antibodies generally provide protection in vivo by blocking the interaction of virus with specific target cells, S-IgA antibodies function by intercepting microbial pathogens before they enter the body. On mucosal surfaces in vivo (anti-gp41HA) S-IgA protect epithelia by cross-linking and agglutinating microorganisms in mucosal secretions, enhancing their entrapment and clearance in mucus, and in some cases by blocking or sterically hindering the microbial surface molecules that mediate epithelial attachment. In addition, S-IgA in the epithelial export pathway may even intercept incoming viral particles. Anti-gp41 IgA antibodies reduce HIV-1 transmission across epithelial monolayers apparently by arresting viral transepithelial transport within apical recycling endosomes. Therefore, binding of S-IgA antibodies to cell-free and cell-associated HIV-1, both of which are present in semen, is expected to reduce the effective infectious viral inoculum at mucosal surfaces.

Experimental Series II

It has been previously showed that systemic priming followed by mucosal boosting of mice with gp41HA could induce gp41-specific IgG in sera and specific IgA in intestinal secretions of mice. In two studies, it has been determined that systemic priming is not required for induction of gp41 antibodies in mucosal secretions or in the circulation of these animals. In these studies, the administration of gp41HA by the nasal route alone was found to generate very high levels of gp41-specific IgG in sera and IgA in secretions. It has also been determined that gp41HA can induce anti-gp41 IgA antibodies in vaginal secretions. The latter finding is particularly important because the presence of anti-gp41 IgA antibodies in vaginal secretions of HIV exposed but uninfected women has been associated with resistance. Thus, the inconclusion of gp41HA in HIV vaccine formulations should be highly effective for induction of gp-41 specific IgA in secretions of both the rectum and the female genital tract, the primary sites of HIV exposures.

Experiment 7

Nasal Administration of gp41HA for Induction of gp41-Specific IgA in Vaginal Secretions Objective:
To determine whether administration of gp41HA by the nasal immunization route alone can induce gp41-specific IgA antibodies in sera and intestinal and vaginal secretions.

Materials And Methods:
Two female Balb/c mice were immunized by the nasal route a total of 3 times, at biweekly intervals, with 50 μg gp41HA plus 1 μg CT. Nasal immunization was performed after sedation of mice by administering these proteins in a total volume of 10 μl (5 μl per naris) using a pipetman. Blood, feces, and vaginal secretions were collected before the first immunization and 10 days after each immunization. Fecal extracts were prepared as described [Mantis et al.]. Vaginal secretions were collected by instilling 50 μl of PBS in the vagina with a pipetman, mixing gently three times, then removing the fluid. The specimens collected were analyzed for the presence of anti-gp41 antibodies by ELISA using recombinant $gp41_{MN}$ (rgp41MN; Immunodiagnostics, Woburn, Mass.) as a coating reagent. Antibody levels were considered significant if they were 2-fold greater than those measured in pre-immunization samples.

Results:
As shown below in Table E1, a nasal prime/boost vaccination strategy with gp41HA was able to induce significant concentrations of gp41-specific IgG antibodies in sera and gp41-specific IgA antibodies in both intestinal and vaginal secretions of mice. In serum, anti-gp41 IgG antibody concentrations were found significantly increased as early as 10 days after the 1st immunization. Induction of anti-gp41 IgA antibodies in mucosal secretions, on the other hand, required 2 nasal immunizations.

TABLE E1

Concentrations of anti-gp41 antibodies in sera and secretions after nasal immunization with gp41HA[a]
anti-gp41 IgG or IgA antibodies

| Mouse | IgG in sera after immunization | | | IgA in fecal extracts after immunization | | | IgA in vaginal washes after immunization | | |
|---|---|---|---|---|---|---|---|---|---|
| | #1 | #2 | #3 | #1 | #2 | #3 | #1 | #2 | #3 |
| A | 102.2 | 378.6 | 425.3 | 0.1 | 0.2 | 1.8 | nd[b] | 0.5 | 2.0 |
| B | 50.8 | 234.3 | 263.7 | nd | 0.1 | 0.7 | nd | 0.2 | 1.3 |

[a]Concentrations shown are μg/ml and significantly greater than those in preimmune specimens.
[b]nd = not detectable (less than 0.02 μg/ml).

Conclusions Drawn from Experiment 7:
Systemic and mucosal immune responses to gp41 can be generated in mice by administering gp41HA with adjuvant solely in the nasal cavity. Gp41HA can be used as an immunogen for generating gp41-specific IgA antibodies in vaginal secretions.

Experiment 8

A gp41HA Nasal Boost in HIV-Vaccinated Mice Increases the Frequency of Vaginal Anti-gp41 IgA Antibody Responses Objective:
To determine whether gp41HA can boost gp41-specific antibody responses in mice previously immunized with aldrithiol-inactivated HIV particles (ALD-HIV).

Materials And Methods:
Female Balb/c mice were nasally-immunized 3 times, at biweekly intervals, with 1 μg CT plus 20 μg ALD-HIV (n=6) or a non-HIV containing aldrithiol-inactivated mock preparation (ALD-mock; n=6). Thirty days after the $3^{rd}$ immunization, all mice were boosted by the nasal route with 50 μg gp41HA plus 1 μg CT. Sera, fecal extracts, and vaginal secretions collected at intervals after each immunization were analyzed by ELISA for the presence of antibodies reactive with recombinant $HIVgp120_{MN}$, $gp41_{MN}$, and $p24_{IIIB}$.

Results:
Mice immunized with ALD-mock did not demonstrate HIV antibodies at any time prior to the nasal boost with gp41HA, as anticipated (data not shown). Mice immunized with ALD-HIV developed p24-specific antibodies in sera and secretions. However, ALD-HIV did not induce anti-gp120 or gp41 antibodies in mice (not shown). This suggests that the doses of ALD-HIV administered may have been too low for generation of antibodies to the less immunogenic gp120 and gp41 proteins compared to p24.

After boosting all mice with gp41HA, IgA antibodies to gp41 were detected in vaginal secretions of 4/6 ALD-HIV immunized mice but only 1/6 ALD-mock immunized mice (Table 2). This suggests that previous immunization with ALD-HIV did establish gp41-specific memory T helper cells or B cells in mice. Interestingly, previous ALD-HIV nasal immunization did not appear to have primed mice for recall responses to gp41 in the systemic compartment or gastrointestinal tract. As shown in Table E2, a similar number of mice in both the HIV naïve and ALD-HIV immunization groups were found to develop serum IgG antibodies to gp41 and intestinal IgA antibodies to gp41 after receiving the gp41HA nasal boost.

TABLE E2

Induction of gp41 antibodies in sera and secretions of ALD-mock versus ALD-HIV-immunized mice after nasal boosting with gp41HA post gp41HA nasal boost fold increases in antibody

| Mouse | gp41-specific IgG in serum[a] | gp41-specific IgA in fecal extract[b] | gp41-specific IgA in vaginal wash[b] |
|---|---|---|---|
| M1[c] | —[d] | 2.9 | — |
| M2 | 2.1 | — | — |
| M3 | 11.5 | — | — |
| M4 | — | — | — |
| M5 | 6.2 | 3.5 | 2.6 |
| M6 | 20.8 | — | — |
| N1 | 12.8 | 2.1 | — |
| N2 | — | — | 3.1 |
| N3 | 13.7 | — | 2.4 |
| N4 | 2.0 | 2.9 | 2.7 |

TABLE E2-continued

Induction of gp41 antibodies in sera and secretions of ALD-mock versus ALD-HIV-immunized mice after nasal boosting with gp41HA post gp41HA nasal boost fold increases in antibody

| Mouse | gp41-specific IgG in serum[a] | gp41-specific IgA in fecal extract[b] | gp41-specific IgA in vaginal wash[b] |
|---|---|---|---|
| N5 | 2.3 | 2.8 | 2.9 |
| N6 | — | — | — |

[a]Ten days after the gp41HA boost; no gp41 antibodies were found before boosting.
[b]Twenty four days after gp41HA boost; no gp41 antibodies present before boosting.
[c]M1-M6 are ALD-mock immunized mice; N1-N6 are ALD-HIV immunized mice.
[d]no significant change when compared to pre-boost levels.

Conclusion Drawn from Experiment 8:

A single gp41HA nasal boost can produce vaginal anti-gp41 IgA antibodies in mice previously immunized with an HIV vaccine candidate containing native gp41. One gp41HA nasal immunization in naïve mice does not appear sufficient for induction of vaginal or intestinal IgA antibodies to gp41. However, the finding that a single nasal dose of gp41HA can induce serum anti-gp41 IgG antibodies in 67% of naïve mice suggests that gp41HA is highly immunogenic because multiple mucosal immunizations with other antigens are typically required for induction of both systemic and mucosal immune responses in mice.

Conclusions Supported by the Data of Experimental Series II

Taken together, the data from experiments 7 and 8 indicate that:

1) Systemic priming with gp41HA is not required for induction of serum or mucosal gp41-specific antibodies. The nasal immunization route alone can be used to generate anti-gp41 IgG antibodies in the circulation and anti-gp41 IgA antibodies in intestinal and vaginal secretions.
2) Gp41HA can be used to generate anti-gp41IgA antibodies in vaginal secretions.
3) Although two nasal immunizations with gp41HA may be required for induction of vaginal and intestinal IgA antibodies to gp41, a single nasal dose of gp41HA can induce serum anti-gp41 IgG antibodies in the majority of vaccinated animals.
4) Gp41HA could be highly effective as a boosting preparation for induction of vaginal anti-gp41 IgA antibodies in HIV vaccine recipients.

The present invention is not to be limited in scope nor restricted in form except by the claims appended hereto.

What we claim is:

1. An isolated fusion protein useful as an immunogen for the induction of HIV-antigen specific IgG and IgA antibodies in-vivo, said fusion protein comprising:
   (i) A first peptidyl region at the N-terminal end of the fusion protein that is a majority portion of an amino acid sequence of HIV envelope glycoprotein gp41 ectodomain;
   (ii) a second peptidyl region at the C-terminal end of the fusion protein that is a part of an amino acid sequence of influenza virus hemagglutinin protein; and
   (iii) an absence of any amino acid residue sequence at the N-terminal end of the fusion protein that includes the GCN4 leucine zipper region or full-length functional variants thereof,
   wherein said fusion protein is soluble at physiological pH in aqueous solutions.

2. An isolated fusion protein useful as an immunogen for the induction of HIV-antigen specific IgG and IgA antibodies in-vivo, said fusion protein comprising:
   (i) A first peptidyl region at the N-terminal end of the fusion protein that comprises the amino acid sequence found at residue position numbers 29-167 of HIV-1$_{IIIB}$ envelope glycoprotein gp41 ectodomain in the HXB2 species;
   (ii) a second peptidyl region at the C-terminal end of the fusion protein that comprises the amino acid sequence at residue position numbers 43-88 of influenza virus hemagglutinin protein subunit 2; and
   (iii) an absence of any amino acid residue sequence at the N-terminal end of the fusion protein that includes the GCN4 leucine zipper region or full-length functional variants thereof,
   wherein said fusion protein is soluble at physiological pH in aqueous solutions.

3. The fusion protein as recited in claim 1 or 2 further comprising a Methionine residue positioned at the N-terminal end of said fusion protein adjacent to said first peptidyl region.

4. The fusion protein as recited in claim 1 or 2 wherein said fusion protein is a recombinant protein expressed by a genetically modified, living host cell.

5. An immunogen useful for the induction of HIV-antigen specific serum IgG and secretory IgA antibodies in vivo, said immunogen comprising:
   A fusion protein that is soluble at physiological pH in aqueous solutions and is comprised of:
   (i) A first peptidyl region at the N-terminal end of the fusion protein that is a majority portion of an amino acid sequence HIV envelope glycoprotein gp41 ectodomain, (ii) a second peptidyl region at the C-terminal end of the fusion protein that is a part of an amino acid sequence of the influenza virus hemagglutinin protein; and (iii) an absence of any amino acid residue sequence at the N-terminal end of the fusion protein that includes the GCN4 leucine zipper region or full-length functional variants thereof; and a biocompatible carrier fluid suitable for carrying and delivering a predetermined aliquot of said fusion protein to a pre-chosen site in a living subject.

6. An immunogen useful for the induction of HIV-antigen specific IgG and secretory IgA antibodies in vivo, said immunogen comprising:

An isolated fusion protein that is soluble at physiological pH in aqueous solutions and is comprised of:

(i) A first peptidyl region at the N-terminal end of the fusion protein that comprises the amino acid sequence at residue position numbers 29-167 of HIV-1$_{IIIB}$ envelope glycoprotein gp41 ectodomain in the HXB2 species;

(ii) a second peptidyl region at the C-terminal end of the fusion protein that comprises the amino acid sequence at residue position numbers 43-88 of influenza virus hemagglutinin protein subunit 2;

(iii) an absence of any amino acid residue sequence at the N-terminal end of the fusion protein that includes the GCN4 leucine zipper region or full-length variants thereof, and a biocompatible carrier fluid suitable for carrying and delivering a predetermined aliquot of said fusion protein to a pre-chosen site in a living subject.

7. The immunogen as recited in claim 5 or 6 wherein said fusion protein further comprises a Methionine residue positioned at the N-terminal end of said fusion protein adjacent to said first peptidyl region.

8. The immunogen as recited in claim 5 or 6 wherein said fusion protein is a recombinant protein expressed by a genetically modified, living host cell.

9. A method to induce HIV-antigen specific serum IgG and secretory IgA antibodies in vivo, said antibody induction method comprising the steps of:

Obtaining an immunogen comprising a fusion protein that is soluble at physiological pH in aqueous solutions and is comprised of:

(i) a first peptidyl region at the N-terminal end of the fusion protein that is a majority portion of an amino acid sequence of HIV envelope glycoprotein gp41 ectodomain, (ii) a second peptidyl region at the C-terminal end of the fusion protein that is a part of an amino acid sequence of influenza virus hemagglutinin protein, (iii) an absence, of any amino acid residue sequence at the N-terminal end of the fusion protein that includes the GCN4 leucine zipper region or full-length functional variants thereof, and (iv) a biocompatible carrier fluid suitable for carrying and delivering a predetermined aliquot of said fusion protein to a pre-chosen anatomic site in the living subject; and systemically administering an aliquot of said immunogen on at least one occasion to the body of the living subject as a primary treatment; and mucosally administering an aliquot of said immunogen on at least one occasion to a pre-chosen mucosal tissue site in the body of the living subject as a secondary treatment.

10. A method to induce HIV-antigen specific serum IgG and secretory IgA antibodies in-vivo, said antibody induction method comprising the steps of:

Obtaining an immunogen comprising a fusion protein which is soluble at physiological pH in aqueous solutions and is comprised of:

(i) A first peptidyl region at the N-terminal end of the fusion protein that comprises the amino acid sequence at residue position numbers 29-167 of HIV-1$_{IIIB}$ envelope glycoprotein gp41 ectodomain in the HXB2 species, (ii) a second peptidyl region at the C-terminal end of the fusion protein that comprises the amino acid sequence at residue position numbers 43-88 of influenza virus hemagglutinin protein subunit 2, (iii) an absence of any amino acid residue sequence at the N-terminal end of the fusion protein that includes the GCN4 leucine zipper region or full-length functional variants thereof, and (iv) a biocompatible carrier fluid suitable for carrying and delivering a predetermined aliquot of said fusion protein to a pre-chosen anatomic site in a living subject;

systematically administering an aliquot of said immunogen on at least one occasion to the body of the living subject as a primary treatment; and mucosally administering an aliquot of said immunogen on at least one occasion to a pre-chosen mucosal tissue site in the body of the living subject as a secondary treatment immunization.

11. The antibody induction method as recited in claim 9 or 10 wherein said immunogen further comprises at least one adjuvant composition dispersed in said carrier fluid.

12. The antibody induction method as recited in claim 9 or 10 wherein said systemic administration is performed as at least one mode of administration selected from the group consisting of intraperitoneal, intramuscular, intravenous, subcutaneous, and subdermal administrations.

13. The antibody induction method as recited in claim 9 or 10 wherein said mucosal administration is performed as at least one mode of administration selected from the group consisting of intranasal and intragastric administrations.

14. The antibody induction method as recited in claim 9 or 10 wherein said systemic administration is repeatedly performed on multiple occasions.

15. The antibody induction method as recited in claim 9 or 10 wherein said mucosal administration is repeatedly performed on multiple occasions.

\* \* \* \* \*